(12) United States Patent
Kim et al.

(10) Patent No.: US 9,976,150 B2
(45) Date of Patent: May 22, 2018

(54) **VECTOR REPLICABLE IN *E. COLI* AND CELL OF GENUS *KOMAGATAEIBACTER*, CELL INCLUDING THE SAME, AND METHOD OF USING THE SAME**

(71) Applicant: Samsung Electronics Co., Ltd., Suwon-si, Gyonggi-do (KR)

(72) Inventors: Jieun Kim, Suwon-si (KR); Jiae Yun, Hwaseong-si (KR); Hongsoon Rhee, Suwon-si (KR); Soonchun Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 15/368,293

(22) Filed: Dec. 2, 2016

(65) Prior Publication Data

US 2017/0166908 A1 Jun. 15, 2017

(30) Foreign Application Priority Data

Dec. 9, 2015 (KR) ........................ 10-2015-0175343

(51) Int. Cl.
*C12N 15/70* (2006.01)
*C12N 15/74* (2006.01)
*C12Q 1/68* (2018.01)

(52) U.S. Cl.
CPC ............. *C12N 15/74* (2013.01); *C12N 15/70* (2013.01); *C12Q 1/6897* (2013.01)

(58) Field of Classification Search
None
See application file for complete search history.

(56) References Cited

U.S. PATENT DOCUMENTS

| | | | |
|---|---|---|---|
| 5,399,496 A | 3/1995 | Fujiwara et al. | |
| 5,962,277 A | 10/1999 | Kunihiko et al. | |
| 6,132,998 A | 10/2000 | Naritomi et al. | |
| RE38,792 E | 9/2005 | Ishihara et al. | |
| 8,021,653 B2 | 9/2011 | Kano et al. | |
| 8,288,127 B2 * | 10/2012 | Schneider | C12N 9/0028 435/471 |
| 8,735,000 B2 | 5/2014 | Imai et al. | |
| 8,883,969 B2 * | 11/2014 | Ide | C12N 15/743 530/350 |
| 2013/0251890 A1 | 9/2013 | Lee et al. | |
| 2016/0351874 A1 | 12/2016 | Kang et al. | |
| 2017/0145469 A1 | 5/2017 | Byun et al. | |
| 2017/0166908 A1 | 6/2017 | Kim et al. | |

FOREIGN PATENT DOCUMENTS

| | | |
|---|---|---|
| JP | 06153964 A | 7/1994 |
| JP | 2005-110597 A | 4/2005 |
| JP | 4989231 B2 | 5/2012 |
| WO | WO 2014-104310 A1 | 7/2014 |

OTHER PUBLICATIONS

Hall et al., "Transformation of Acetobacter xylinum with plasmid DNA by electroporation", Plasmid, 28(3): 194-200 (1992).
Nakai et al., "Formation of Highly Twisted Ribbons in a Carboxymethylcellulase Gene-Disrupted Strain of a Cellulose-Producing Bacterium", *Journal of Bacteriology*, 195(5): 958-964 (2013).
Tonouchi et al., A Host-Vector System for a Cellulose-Producing *Acetobacter* Strain, *Bioscience, Biotechnology, and Biochemistry*, 58(10): 1899-1901 (1994).
Close, et al., "Design and Development of Amplifiable Broad-Host-Range Cloning Vectors: Analysis of the vir Region of *Agrobacterium tumefaciens* Plasmid pTiC58", *Plasmid*, 12; 111-118 (1984).
European Patent Office, Extended European search report for Application No. 162024632-1404 dated Apr. 21, 2017, 12 pages.
Deng et al. "Identification and Characterization of Non-Cellulose-Producing Mutants of *Gluconacetobacter hansenii* Generated by Tn5 Transposon Mutagenesis", *Journal of Bacterilogy*, vol. 195, pp. 5072-5083 (2013).
Deng et al. "Isolation and Characterization of Two Cellulose Morphology Mutants of *Gluconacetobacter hansenii* ATCC23769 Producing Cellulose with Lower Crystallinity", *PLOS One*, DOI:10:1371, 18 pages (2015).
Florea et al., Engineering control of bacterial cellulose production using a genetic toolkit and a new cellulose-producing strain, Proceedings National Academy of Sciences PNAS, 113(24): E3431-E3440 (2016).
Naoto Tonouchi et al., "A Host-Vector System for a Cellulose-Producing Acetobacter Strain", *Bioscience Biotechnology Biochemistry*, vol. 58, No. 10, pp. 1899-1901 (1994).
Nakai et al, "Control of expression by the cellulose synthase (bcsA) promoter region from *Acetobacter xylinum* BPR 2001", *Gene*, vol. 213, No. 1-2 (1998).
Lisdiyanti Puspita et al., Reclassification of *Gluconacetobacter hansenii* strains and proposals of *Gluconacetobacter saccharivorans* sp. nov. and *Gluconacetobacter nataicola* sp. nov, *International Journal of Systematic and Evolutionary Microbiology*, vol. 56, pp. 2101-2111 (2006).
Deng et al., "Identification and Characterization of Non-Cellulose-Producing Mutants of *Gluconacetobacter hansenii* Generated by Tn5 Transposon Mutagenesis," *Journal of Bacteriology*, vol. 195, No. 22, pp. 5072-5083 (2013).

(Continued)

*Primary Examiner* — James S Ketter
(74) *Attorney, Agent, or Firm* — Leydig, Voit & Mayer, Ltd.

(57) ABSTRACT

Provided are a vector replicable in *E. coli* and a cell of the genus *Komagataeibacter*, a cell including the same, a method of producing a target protein using the cell, or a method of evaluating a candidate promoter using the cell.

21 Claims, 3 Drawing Sheets

(56) References Cited

OTHER PUBLICATIONS

Tonouchi et al., "A Host-Vector System for a Cellulose-Producing Acetobacter Strain," *Biosci Biotechnol Biochem*, 58 (10), pp. 1899-1901 (1994).

* cited by examiner

VECTOR REPLICABLE IN *E. COLI* AND CELL OF GENUS *KOMAGATAEIBACTER*, CELL INCLUDING THE SAME, AND METHOD OF USING THE SAME

CROSS-REFERENCE TO RELATED APPLICATION

This application claims the benefit of Korean Patent Application No. 10-2015-0175343, filed on Dec. 9, 2015, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 49,819 Byte ASCII (Text) file named "726011_ST25.TXT-Revised" created on Feb. 10, 2017.

BACKGROUND

1. Field

The present disclosure relates to a vector replicable in *E. coli* and a cell of the genus *Komagataeibacter*, a cell comprising the vector, a method of producing a target protein using the cell, and a method of evaluating a candidate promoter using the cell, as well as related methods and compositions.

2. Description of the Related Art

Cellulose produced by culturing microorganisms exists as a primary structure of β-1,4 glucan, which are polysaccharides composed of glucose subunits. The β-1,4-glucans form a network structure of fibril aggregates. This cellulose is also called 'biocellulose' or 'microbial cellulose.'

Unlike plant cellulose, microbial cellulose is pure cellulose entirely free of lignin or hemicelluloses. The fiber width of microbial cellulose is 100 nm, which is less than that of plant cellulose. Microbial cellulose has wetting and water absorption properties, high strength, high elasticity, and high heat resistance, etc. Due to these properties, microbial cellulose has been developed and applied to a wide variety of fields, such as beauty products, medical fields, dietary fibers, acoustic diaphragms, functional films, etc.

Several cellulose-producing strains have been reported, including *Acetobacter, Agrobacteria, Rhizobia*, and *Sarcina*. Among these, *Komagataeibacter xylinum* (also called '*Acetobacter xylinum*') is known as a particularly excellent strain. A static aerobic culture of these microbes produce a three-dimensional network of cellulose formed as a thin film on the surface of the culture medium.

To improve the utility of these strains, however, shuttle vectors are needed to provide more efficient genetic manipulation. Whereas a cloning vector requires only a replication origin for maintenance of a plasmid form within a strain, a selection marker gene for selection of a strain retaining the vector, and a multi-cloning site (MCS) for cloning of a foreign gene, shuttle vectors should be able to maintain a plasmid in a plurality of strains. Typically, shuttle vectors can be used to clone plasmid in *E. coli* and transform another strain. There is a need for shuttle vectors that are able to replicate in *E. coli* and a cell of the genus *Komagataeibacter*, particularly *Komagataeibacter xylinum*.

SUMMARY

Provided is a vector useful for replication in both *E. coli* and at least one species of *Komagataeibacter*. In one aspect, the vector comprises a pSa-ori comprising SEQ ID NO: 1, a pUC-ori comprising SEQ ID NO: 3, and a selection marker gene.

Also provided is a cell comprising the vector, wherein the cell is *E. coli* or a cell of the genus *Komagataeibacter*.

Further provided is a method of producing a target protein by culturing a cell of the genus *Komagataeibacter* comprising the vector that is replicable in *E. coli* and the cell of the genus *Komagataeibacter*.

Still another aspect provides a method of evaluating promoter activity in a cell of the genus *Komagataeibacter*. The method comprises culturing a first cell of the genus *Komagataeibacter* comprising a first vector that replicates in *E. coli* and the *Komagataeibacter* cell, wherein the first vector comprises a candidate promoter, a first reporter gene, and a transcription terminator which are operably linked to each other; culturing a second cell of the genus *Komagataeibacter* comprising a second vector that replicates in *E. coli* and the *Komagataeibacter* cell, wherein the second vector comprises a control promoter, a second reporter gene, and a transcription terminator which are operably linked to each other; and comparing expression of the first and second reporter genes to evaluate the activity of the candidate promoter relative to the control promoter.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
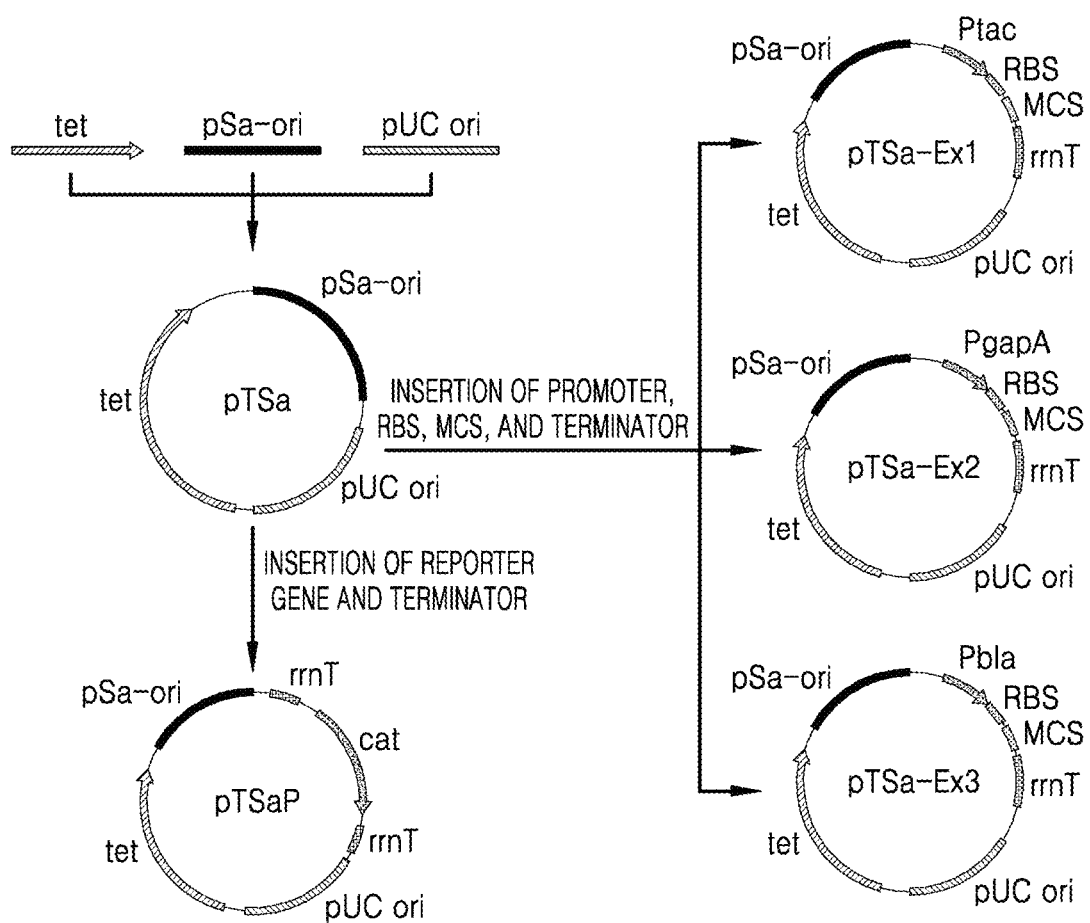
FIG. 1 is a diagram showing the construction process of a pTSaP vector, a pTSa-Ex1 vector, a pTSa-Ex2 vector, and a pTSa-Ex3 vector.

An aspect of the present disclosure provides a vector replicable in *E. coli* and a at least one cell of the genus *Komagataeibacter*, the vector including a nucleotide sequence of SEQ ID NO: 1 (pSa ori), a nucleotide sequence of SEQ ID NO: 3 (pUC ori), and a selection marker gene.

SEQ ID NO: 1 (pSa ori) is part of the nucleotide sequence of a pSa origin sequence which is a replication origin of a broad host vector pUCD2 of SEQ ID NO: 2, and enables the vector to replicate in cells of the genus *Komagataeibacter*. The nucleotide sequence of SEQ ID NO: 3 (pUC ori) enables the vector to replicate in cells of the genus *Escherichia*.

In the vector, the selection marker gene (gene encoding a selection marker or selectable marker) may be any gene that encodes a gene product permitting selection of a cell harboring the gene. A great variety of selection markers are routinely used in the art. For instance, a selection marker gene can be a gene that permits growth of the cell harboring said gene under conditions that would otherwise inhibit growth of a cell lacking said gene. For example, the selection marker gene may be an antibiotic resistance gene or a gene producing an essential nutrient (a nutrient necessary for cell survival). The antibiotic may include tetracycline, chloramphenicol, kanamycin, or ampicillin. The antibiotic resistance gene may be a gene encoding beta lactamase, or a gene encoding chloramphenicol acetyl transferase, tetA or a gene encoding chloramphenicol acetyl transferase, tetA genes of classes A (including RP1, RP4 or Tn1721 derivative), B (Tn10 derivative) and C (pSC101 or pBR322 derivative) encoding a tetracycline efflux system. The tetracycline resistance gene may have a nucleotide sequence of SEQ ID NO: 4. The gene producing an essential nutrient may be a gene involved in production of amino acids, nucleosides, nucleotides, nucleic acid bases or proteins.

The vector may further include a promoter, a ribosomal binding site (RBS), a multi-cloning site (MCS), or a transcription terminator; or the vector may include two, three, or all four of these elements. Furthermore, any two or more of these elements (the promoter, the ribosomal binding site, the multi-cloning site, and the transcription terminator), if included, can be operably linked to each other.

Any suitable promoter, RBS, MCS, or terminator can be used. The promoter may have, for example, a nucleotide sequence of SEQ ID NO: 5 (tac promoter), 6 (gapA promoter), or 7 (bla promoter). The RBS may, for instance, be derived from a cell of the genus *Komagataeibacter*. The ribosomal binding site may have a nucleotide sequence of SEQ ID NO: 8. The multi-cloning site (MCS) may have any suitable number of restriction enzyme sites (e.g., two or more, for example, 3, 4, 5, 6, 7, or 8 restriction enzyme sites). The MCS may have a nucleotide sequence of SEQ ID NO: 9. An exemplary MCS comprises restriction recognition sequences of 8 restriction enzymes: KpnI, EcoRI, SmaI, BamHI, XbaI, SalI, PstI, and HindIII. An example of a transcription terminator is one comprising a nucleotide sequence of SEQ ID NO: 10.

Specific examples of vectors include a pTSa-Ex1, pTSa-Ex2, or pTSa-Ex3 vector having a nucleotide sequence of SEQ ID NO: 12, 13, or 14.

As used herein, the term "operably linked" refers to an arrangement of elements in the vector that in some way connects the regulation, transcription or translation of one nucleic acid sequence to the regulation, transcription, or translation of another nucleic acid sequence. For instance, a reporter gene may be a gene operably linked to a regulatory sequence (e.g., promoter) if the promoter drives expression of the reporter gene. Similarly, the reporter gene may be operably linked to another gene of interest (e.g., a gene encoding a target protein) so they are co-expressed when a cell is transformed with the vector.

The vector also can include a reporter gene. The reporter gene may be a gene that confers a characteristic of being easily identified or measured on an organism expressing the gene. The reporter gene may be used as an indication of whether a certain gene has been taken up by or expressed in the cell. The reporter gene may be a fluorescent or luminescent protein. For example, the reporter gene may be a jellyfish green fluorescent protein (GFP), luciferase, or a red fluorescent protein. The reporter gene may be a lacZ gene encoding β-galactosidase, or a cat gene encoding chloramphenicol acetyltransferase (CAT). The transcription terminator may be derived from *E. coli*, or a cell of the genus *Komagataeibacter*. For example, the reporter gene may have a nucleotide sequence of SEQ ID NO: 16.

The vector may have a nucleotide sequence of SEQ ID NO: 15 (pTSaP). The vector may be replicable in *E. coli* and a cell of at least one species of the genus *Komagataeibacter*, for example, *Komagataeibacter xylinus*. Other species include, for instance, *Komagataeibacter europaeus*, *Komagataeibacter hansenii*, *Komagataeibacter intermedius*, *Komagataeibacter kakiaceti*, *Komagataeibacter kombuchae*, *Komagataeibacter maltaceti*, *Komagataeibacter medellinensis*, *Komagataeibacter nataicola*, *Komagataeibacter oboediens*, *Komagataeibacter rhaeticus*, *Komagataeibacter saccharivorans*, *Komagataeibacter sucrofermentans*, and *Komagataeibacter swingsii*.

An embodiment of the invention is a cell of the genus *Komagataeibacter* or an *E. coli* cell comprising the vector described herein, which is replicable in *E. coli* and the cell of the genus *Komagataeibacter*. The vector further comprises a promoter, a ribosomal binding site, a gene of encoding a target protein, and a transcription terminator, which are operably linked to each other. All aspects of the vector are as described above.

The target protein encoded by the vector (gene of interest in the vector) may be any protein. The target protein may be a non-glycosylated protein which may be expressed in the cell of the genus *Komagataeibacter*. The target protein may be an enzyme involved in synthesis of bacterial cellulose. The synthetic pathway of bacterial cellulose can be that shown in FIG. 3. Examples of target proteins include permease, glucose kinase (GLK), phosphoglucomutase (PGM), UDP-glucose pyrophosphorylase (UGP), or cellulose synthase (CS), and examples of genes of interest to be included in the vector include genes encoding these proteins. The gene encoding the target protein also may be a *Xanthomonas campestris* (Xc) xanA gene, a *Komagataeibacter xylinus* (Kx) pgm gene, an *E. coli* (EC) galU gene, or a *Xanthomonas campestris* (Xc) UGP gene. The cell may produce cellulose or have an ability to produce cellulose.

Another embodiment provides a method of producing a target protein from a cell of the genus *Komagataeibacter*. The method comprises culturing a cell of the genus *Komagataeibacter* comprising the vector provided herein in a medium to obtain a culture. The vector is replicable in *E. coli* and the cell of the genus *Komagataeibacter*, and includes a promoter, a ribosomal binding site, a gene encoding a target protein, and a transcription terminator, which are operably linked to each other. Upon culturing the cell, the target protein is produced.

In the method of the present invention, the culturing may be performed according to general methods known in the art. A medium used for the culturing may include, as a sugar source, sugar and carbohydrate, such as glucose, saccharose, lactose, fructose, maltose, starch, and cellulose; oil and fat, such as soybean oil, sunflower oil, castor oil, and coconut oil; a fatty acid, such as palmitic acid, stearic acid, and linolenic acid; an alcohol, such as glycerol and ethanol; and an organic acid, such as acetic acid, singly or in a mixture. The medium may include, as a nitrogen source, for example, peptone, yeast extract, meat extract, malt extract, corn steep liquor, soy meal and urea, or an inorganic compound, e.g., ammonium sulfate, ammonium chloride, ammonium phosphate, ammonium carbonate and ammonium nitrate, singly or in a mixture. The medium may include, as a phosphorous source, for example, potassium dihydrogen phosphate, dipotassium hydrogen phosphate, or a corresponding sodium-containing salt thereof. The medium may include, for example, a metal salt, such as magnesium sulfate or iron sulfate, which is essential for growth. Also, in the culturing, substances essential for growth, such as amino acids and vitamins, or suitable precursors may be added to the culture. Those components may be added to the culture in a proper manner, for example, in a batch or continuous manner during the culturing. The culturing may be performed under aerobic conditions.

The method of producing a target protein can be used for any purpose, such as for producing a target product. The target product may be, for example, cellulose.

The method may further include separating the target protein or target product from the culture thus obtained. The separating may vary depending on the target product. For example, if the target product is cellulose, the separating may include centrifugation of the culture or physical separation of cellulose at the interface between the culture and air.

Still another aspect provides a method of evaluating a promoter activity in a cell of the genus *Komagataeibacter*. The method includes culturing the cell of the genus *Komagataeibacter* including a first vector as described herein in a medium to express a first reporter gene. In addition to the nucleotide sequence of SEQ ID NO: 1 (pSa ori), the nucleotide sequence of SEQ ID NO: 3 (pUC ori), and the selection marker gene, the first vector also includes a candidate promoter, the first reporter gene and a transcription terminator which are operably linked to each other. The method also comprises culturing a second cell of the genus *Komagataeibacter* including a second vector in a medium to express a second reporter gene. In addition to the nucleotide sequence of SEQ ID NO: 1 (pSa ori), the nucleotide sequence of SEQ ID NO: 3 (pUC ori), and the selection marker gene, the second vector also includes a control promoter, the second reporter gene, and a transcription terminator which are operably linked to each other. The method comprises measuring the expression level (products) of the first and second reporter genes from the first and second cells; and determining a transcription-inducing activity of the candidate promoter by comparing levels of the reporter genes which are expressed from the candidate promoter and the control promoter.

The candidate promoter may be any nucleotide sequence which is predicted to have a promoter activity. The candidate promoter may be any promoter which is known to have a promoter activity. The culturing is the same as described above. The first and second reporter genes may be the same or different. In one embodiment, one or both reporters may be a chloramphenicol acetyltransferase (CAT) gene.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

Example 1: Preparation of Shuttle Vector Replicable in *E. Coli* and Cell of the Genus *Komagataeibacter*

A preparation process of a pTSa vector including a partial sequence (a nucleotide sequence of SEQ ID NO: 1) of a pSa origin sequence of a broad host vector pUCD2, a pUC origin sequence having a nucleotide sequence of SEQ ID NO: 3, which is an *E. coli* replication origin, and a tetracycline gene (tet) having a nucleotide sequence of SEQ ID NO: 4 as a selection marker gene is as follows. First, PCR was performed using a pUC19 vector as a template and a set of primers of nucleotide sequences of SEQ ID NOS: 22 and 23 to obtain a vector framework. PCR was performed using a synthetic tetracycline gene as a template and a set of primers of nucleotide sequences of SEQ ID NOS: 24 and 25 to obtain the tetracycline gene. A tetracycline gene-introduced pUC19 vector was prepared by a primary In-Fusion® cloning method (In-Fusion® HD Cloning Plus kit: cat no: 638909: Clontech). Next, PCR was performed using the tetracycline gene-introduced pUC19 vector as a template and a set of primers of nucleotide sequences of SEQ ID NOS: 26 and 27 to obtain a pUC19-Tet vector framework. PCR was performed using the synthetic pSa ori gene as a template and a set of primers of nucleotide sequences of SEQ ID NOS: 28 and 29 to obtain the pSa ori sequence. A pTsa vector (SEQ ID NO: 11) was prepared by a secondary In-Fusion® cloning method.

The pTSa vector and a prepared rrnT-BglIII recognition site-cat-rrnT sequence were linked to each other by the In-Fusion® cloning method to prepare a pTSaP vector (SEQ ID NO: 15). Here, rrnT represents a terminator sequence of an *E. coli* global rrnB gene, BglIII recognition site represents a sequence having a BglIII restriction enzyme recognition site, and cat represents a chloramphenicol acetyltransferase gene. In the pTSaP vector, the BglIII restriction enzyme recognition site was operably linked to the reporter gene. Therefore, the vector may be used to examine a promoter activity of a candidate promoter. In other words, the pTSaP vector is a vector for promoter exploration.

Further, a promoter sequence-ribosomal binding site (RBS) (SEQ ID NO: 8)-multiple cloning site (MCS)-rrnT sequence was linked between the pSa ori sequence and the pUC ori sequence in the pTSa vector to prepare a vector for gene expression. RBS was derived from *Komagataeibacter xylinus*. As the promoter sequence, a tac promoter (Ptac) (SEQ ID NO: 5), a gapA promoter (PgapA) (SEQ ID NO: 6), and a bla promoter (Pbla) (SEQ ID NO: 7) were used, respectively. The MCS included restriction recognition sequences of 8 restriction enzymes, KpnI, EcoRI, SmaI, BamHI, XbaI, SalI, PstI, and HindIII. PgapA was a *Komagataeibacter xylinus* GapA promoter. The pTSa vector and the prepared Ptac-RBS-MCS-rrnT sequence, PgapA-RBS-MCS-rrnT sequence, or Pbla-RBS-MCS-rrnT sequence were linked to each other by the In-Fusion® cloning method to prepare a pTSa-Ex1 vector (SEQ ID NO: 12), a pTSa-Ex2 vector (SEQ ID NO: 13), or a pTSa-Ex3 vector (SEQ ID NO: 14), respectively. The pTSa-Ex1 vector was prepared as follows: PCR was performed using the pTSa vector as a template and a set of primers of nucleotide sequences of SEQ ID NOS: 30 and 31 to obtain the vector framework. PCR was performed using the pTac15K vector as a template and a set of primers of nucleotide sequences of SEQ ID NOS: 32 and 33 to obtain the tac promoter sequence. PCR was performed using the pTac15K vector as a template and a set of primers of nucleotide sequences of SEQ ID NOS: 34 and 35 to obtain the RBS-MCS-rrnt sequence. These products thus obtained were linked to each other by the In-Fusion® method to prepare the pTSa-Ex1 vector (SEQ ID NO: 12).

The pTSa-Ex2 vector was prepared as follows: PCR was performed using the pTSa vector as a template and a set of primers of nucleotide sequences of SEQ ID NOS: 36 and 37 to obtain the vector framework. PCR was performed using genomic DNA of *Komagataeibacter* as a template and a set of primers of nucleotide sequences of SEQ ID NOS: 38 and 39 to obtain the PGapA promoter sequence. PCR was performed using the pTac15K vector as a template and a set of primers of nucleotide sequences of SEQ ID NOS: 34 and 35 to obtain the RBS-MCS-rrnt sequence. These products thus obtained were linked to each other by the In-Fusion® method to prepare the pTSa-Ex2 vector (SEQ ID NO: 13).

The pTSa-Ex3 vector was prepared as follows: PCR was performed using the pTSa-Ex1 vector as a template and a set of primers of nucleotide sequences of SEQ ID NOS: 40 and 41, and the products were linked to each other by the In-Fusion® method to obtain the pTSa-Ex3 vector (SEQ ID NO: 14). That is, the promoter of pTsa-Ex1 was replaced by a bla promoter.

FIG. 1 is a diagram showing a construction process of the pTSaP vector, the pTSa-Ex1 vector, the pTSa-Ex2 vector, or the pTSa-Ex3 vector.

Further, the pTSa vector was introduced into an *E. coli* Top10F strain by transformation, and cultured on a LB medium plate (Luria-Bertani medium: 1% tryptone, 1% NaCl, 0.5% yeast extract and 1.5% agar) containing 15 ug/mL of tetracycline (LB+) for 16 hours. As a result, formation of pTSa vector-including *E. coli* colonies was observed, indicating that the pUC origin operated well in *E. coli*.

Figure 2:
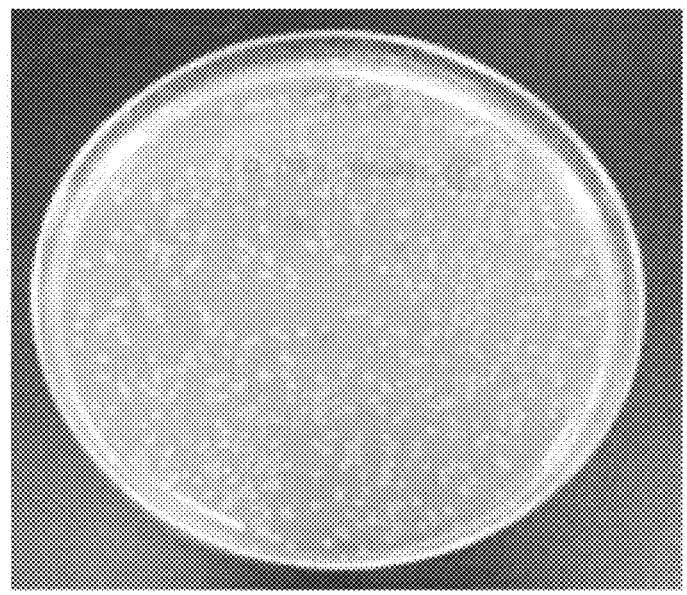
FIG. 2 shows result of formation of *E. coli* colonies having a pTSa vector including a pUC origin sequence.

FIG. 2 shows result of formation of *E. coli* colonies having the pTSa vector including the pUC origin sequence.

Example 2: Expression of Protein and Exploration of Promoter Using Shuttle Vector Replicable in *E. coli* and Cell of the Genus *Komagataeibacter*

In this Example, it was examined whether the vectors prepared in Example 1 were replicable in both *E. coli* and the cell of the genus *Komagataeibacter*, and the vectors were used in protein expression and promoter exploration.

(1) Activity as Expression Vector

To prepare a pTSa-EX1 vector containing a foreign gene involved in a cellulose biosynthetic pathway, pTSa-EX1 prepared in Example 1 was digested with PstI enzyme. As the foreign gene involved in the cellulose biosynthetic pathway, *E. coli* galP (EC.galP) gene was used. An insert galP gene was amplified by PCR using primers having nucleotide sequences of SEQ ID NOS: 47 and 48, which contain a region of homology with the pTSa-EX1 vector. The EC,galP PCR product was linked to the vector digested with PstI by the In-Fusion® method to produce the vector pTSa-EX1-EC.galP.

Figure 3:
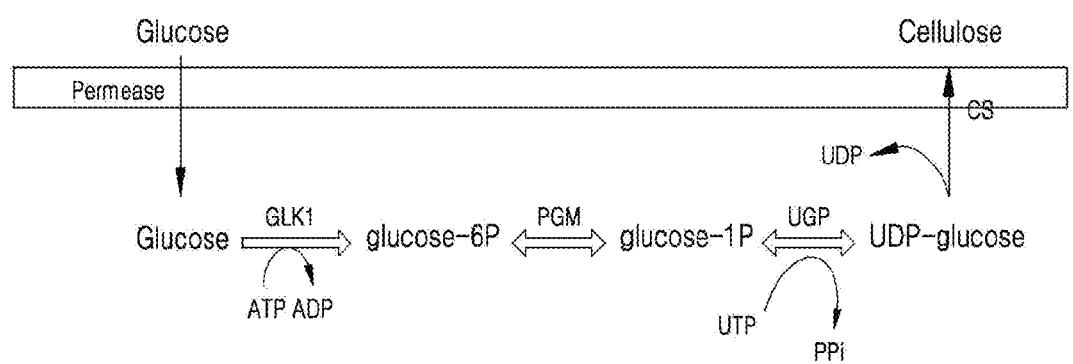
FIG. 3 shows an example of a cellulose synthetic pathway in *K. xylinus*.

FIG. 3 shows an example of the cellulose synthetic pathway in *K. xylinus*. The enzymes depicted in FIG. 3 are glucose kinase (GLK), phosphoglucomutase (PGM), UDP-glucose pyrophosphorylase (UGP), and cellulose synthase (CS).

Next, pTSa-EX1-EC.galP or empty vector (pTSa-EX1) was transformed into *K. xylinus* (Korean Culture Center of Microorganisms, KCCM 41431) by electroporation. Each of the transformed *K. xylinus* strains was inoculated into a 250 ml flask containing 50 ml of an HS medium (0.5% peptone, 0.5% yeast extract, 0.27% $Na_2HPO_4$, 0.15% citric acid, and 2% glucose), and cultured at 30° C. under stirring at 200 rpm for 24 hours. The cultures were centrifuged at 4000 rpm for 10 minutes to collect cellulose at the interface between the culture and air, and cells. The cellulose and cells were washed with deionized water once and with 0.5% NaOH once to collect only cellulose. Thereafter, the cellulose was dried in a dry oven at 60° C. for 16 hours, and then weighed.

Figure 4:
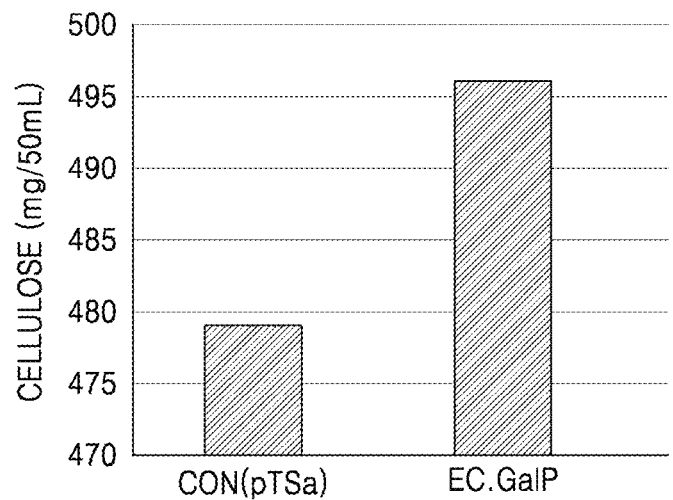
FIG. 4 shows the amount of cellulose produced from *K. xylinus* transformed with either a pTSa-EX1 empty vector (CON(pTSa)) or with a pTSa-EX1 vector comprising an *E. coli* galP gene (EC.GalP)

FIG. 4 shows the amount of cellulose produced from *K. xylinus* transformed with either empty vector (CON(pTSa)) or with pTSa-EX1-EC.galP. As shown in FIG. 4, cells transformed with pTSa-EX1 produced 479 mg of cellulose/50 ml, whereas cells transformed with pTSa-EX1-EC.galP showed a larger cellulose production amount of 496 mg/50 ml, indicating that pTSa-EX1 operated well in *K. xylinus*.

(2) Examination of Copy Number and Plasmid Stability of pTSa Vector

Each of the pTSa vectors prepared in Example 1 was transformed into *K. xylinus* KCCM 41431 (purchased from KCCM) by electroporation. Each of the transformed *K. xylinus* strains was inoculated into a 50 ml tube containing 10 ml of an HS medium containing 0.2% cellulase and 10 ug/mL of tetracycline, and cultured at 30° C. under stirring at 200 rpm for 24 hours.

Cells were isolated from the culture and plasmid DNA and genomic DNA were prepared using a Qiagen kit. BcsA (bacterial cellulose synthase A) exists as a single copy per genome, and thus, its qRT-PCR value per copy was compared with the qRT-PCR value of a copy of tetracycline to determine a copy number of the final pTSa vector. qRT-PCR was performed using nucleotide sequences of SEQ ID NO: 43 and 44, or nucleotide sequences of SEQ ID NO: 45 and 46 as primers and genomic DNA separated from the cells as a template for BcsA, and plasmid DNA as a template for tetracycline.

As a result of qRT-PCR, a copy number of the pTSa vector in *K. xylinus* is shown in Table 1. Table 1 shows copy numbers of commercially available pUCD2 and pTSa of the present Example in *K. xylinus*. As shown in Table 1, the pTSa vector had a medium copy number of 60 copies or higher.

Further, in order to examine stability of the vector, pTSa vector-containing *K. xylinus* was inoculated in the HS medium without tetracycline, and then spread on a plate containing the HS medium with tetracycline over time to examine the number of colonies. As a result, colony formation of the pTSa vector was observed on the HS medium with tetracycline at day 1, day 2, and day 3, and no colony formation was observed at day 4 or later. In contrast, the pUCD2-containing strain lost the plasmid after 1 day, and thus no colony formation was observed on the HS medium with tetracycline. That is, the pTSa vector showed higher stability.

TABLE 1

| Vector | Replication origin | Copy number | Stability | Reference |
|---|---|---|---|---|
| pUCD2 | Foreign | low (<10) | low | Commercially available data |
| pTSa | Foreign | medium (>60) | high | This application |

(3) Selection of Promoter Using pTSaP Vector

Three kinds of promoters which may be utilized in gene overexpression were explored in acetic acid bacteria, especially, microbial cellulose-producing bacteria of the genus *Komagataibacter*. All of these promoters were derived from a genome of *Komagataibacter xylinus* KCCM 41431 which is a natural microbial cellulose-producing bacterium, and they had strength useful for gene overexpression.

(3.1) Exploration of Promoter

The genomic DNA of *K. xylinus* KCCM 41431 was extracted, and partially digested with Sau3AI. Of digestion products, DNA fragments having a size of 0.5 to 1.5 kb were extracted from a 1% agarose gel. Each of the extracted DNA fragments was ligated to a promoter exploration vector, pTSaP (SEQ ID NO: 15), which was digested with BglII.

These vectors were transformed into *E. coli* Top10 strain (Invitrogen), and then plated on Luria Bertani (LB) solid media containing 10 ug/ml of tetracycline and 5 ug/ml of chloramphenicol. Plasmids were isolated from pooled colonies, and *K. xylinus* KCCM 41431 was transformed with each of the plasmid by electroporation, and then plated on a HS solid medium containing 5 ug/ml tetracycline to obtain colonies. In pTSaP, the inserted genomic DNA and a reporter gene, chloramphenicol acetyltransferase (cat), were operably linked. In pTSaP, a replication origin pSa ori which allows initiation of replication in cells of the genus *Komagataibacter*, a tetracycline resistance gene, an *E. coli* replication origin pUC ori, and the reporter gene cat were operably linked to a transcription terminator.

*K. xylinus* KCCM 41431 colonies thus obtained were passaged on HS solid media containing 5 ug/ml of tetracycline and 120 ug/ml of chloramphenicol, respectively. Plasmids were isolated from *K. xylinus* KCCM 41431 colonies which were successfully passaged by culturing at 30° C. for 48 hours or longer. Then, the plasmids were used as a template and polynucleotides of SEQ ID NOS: 17 and 18 were used as primers to perform sequencing.

As a result of the sequencing, a sequence of DNA cloned into the BglII site of the pTSaP vector was revealed, and the obtained promoters were designated as P1, P2, and P3. The P1, P2, and P3 promoters have nucleotide sequences of SEQ ID NOS: 19, 20, and 21, respectively.

(3.2) Evaluation of Promoter Strength

Promoter activity of the inserted genomic DNA was determined by measuring the strength of the CAT reporter activity. With regard to control groups, pTSaP introduced without the genomic DNA was used as a negative control group, and pTSaP containing a generally used tac promoter (SEQ ID NO: 5) was used as a positive control group.

CAT activity was determined by a CAT assay that measures acetylated chloramphenicol, and the CAT assay was performed as follows. Acetyl-CoA was reacted with chloramphenicol in the presence of CAT enzyme and 5,5'-dithio-bis (2-nitrobenzoic acid (DTNB) to produce acetyl-chloramphenicol and CoA. CoA reacts with DTNB to be converted into 5-thio-2-nitrobenzoate (TNB) which has an absorbance at 412 nm. *K. xylinus* colonies obtained in section (3.1) and control groups transformed with pTSaP empty vector or pTSaP containing the tac promoter were cultured in HS liquid media containing tetracycline (5 ug/ml) and cellulose (0.5%, Sigma C2730) at 30° C. for 24 hours under stirring at 220 rpm. The bacteria were harvested and suspended in PBS buffer, and then disrupted by sonication, followed by centrifugation. A supernatant was collected and a crude protein was obtained. Next, 10 ug of the crude protein per 1 ml of a reaction solution was mixed and reacted with acetyl-CoA (200 ug/mL), chloramphenicol (100 ug/mL), and DTNB (50 mg/mL), and absorbance at 412 nm was measured over time. The measured absorbance was applied to the following equation to calculate the CAT activity:

$$\text{activity(units/ml enzyme)} = (\Delta 412 \text{ nm/min test} - \Delta 412 \text{ nm/min Blank})(df)/(0.0136) \text{ (df: dilution factor)}$$

Figure 5:
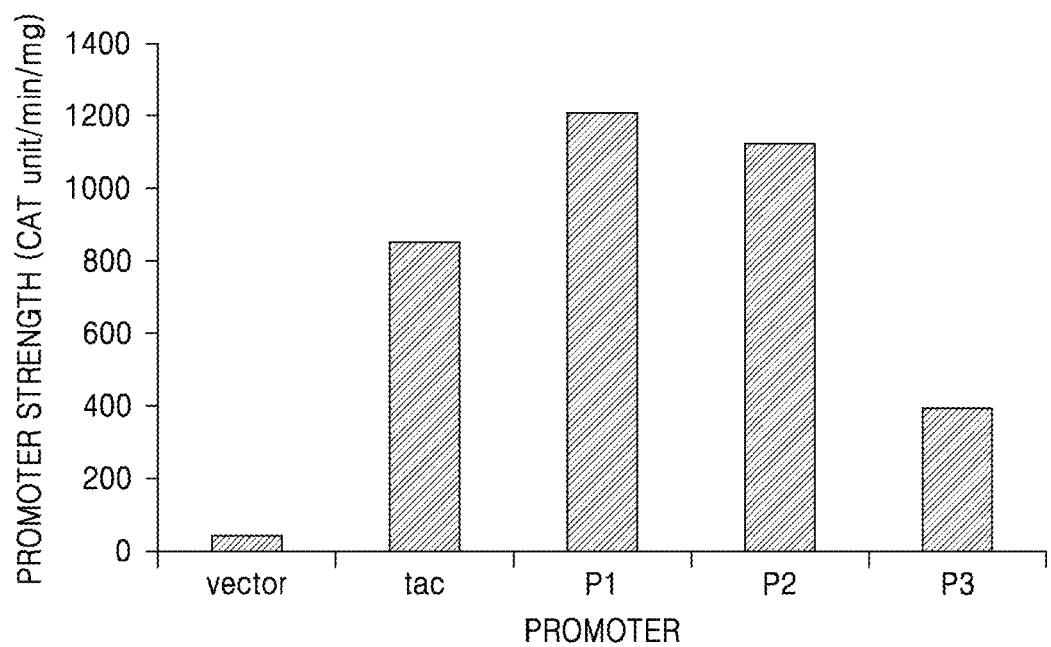
FIG. 5 shows the results of a CAT assay.

FIG. 5 shows the result of CAT assay. In FIG. 5, vector (negative control group), tac (positive control group), P1, P2, and P3 on the horizontal axis represent the pTSaP vector introduced without the genomic DNA, the pTSaP vector introduced with the tac promoter, and the pTSaP vector introduced with the promoter of SEQ ID NO: 19, 20, or 21, respectively. As shown in FIG. 5, P1, P2, and P3 showed strength 1.41 times, 1.31 times, and 0.46 times higher than that of the positive control group, respectively. They also showed marked expression-improving effects, compared to the negative control group. These results suggest that the pTSaP vector efficiently replicates in *K. xylinus* and efficiently induces gene expression.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A vector replicable in *E. coli* and a cell of at least one species of the genus *Komagataeibacter*, the vector comprising a pSa-ori consisting of SEQ ID NO: 1, a pUC-ori comprising SEQ ID NO: 3, and a selection marker gene.

2. The vector of claim 1, wherein the selection marker gene is an antibiotic resistance gene or a gene producing an essential nutrient.

3. The vector of claim 1, further comprising one or more of a promoter, a ribosomal binding site (RBS), a multi-cloning site (MCS), and a transcription terminator.

4. The vector of claim 1, further comprising two or more of a promoter, a ribosomal binding site, a multi-cloning site, and a transcription terminator which are operably linked to each other.

5. The vector of claim 1, wherein the vector comprises a tetracycline resistance gene.

6. The vector of claim 5, wherein the tetracycline resistance gene comprises SEQ ID NO: 4.

7. The vector of claim 3, wherein the vector comprises a promoter comprising SEQ ID NO: 5, 6, and/or 7.

8. The vector of claim 3, wherein the vector comprises a ribosomal binding site comprising SEQ ID NO: 8.

9. The vector of claim 3, wherein the vector comprises a multi-cloning site (MCS) comprising SEQ ID NO: 9.

10. The vector of claim 3, wherein the vector comprises a transcription terminator comprising SEQ ID NO: 10.

11. The vector of claim 1, wherein the vector further comprises SEQ ID NO: 12, 13, or 14.

12. The vector of claim 1, comprising a multi-cloning site, a reporter gene, and a transcription terminator which are operably linked to each other.

13. The vector of claim 12, wherein the reporter gene comprises a chloramphenicol acetyltransferase (CAT) gene.

14. The vector of claim 12, wherein the vector comprises SEQ ID NO: 15.

15. The vector of claim 1, wherein the cell is a *Komagataeibacter xylinus* cell.

16. A cell comprising the vector of claim 1, wherein the cell is an *E. coli* or *Komagataeibacter* cell.

17. The cell of claim 16, wherein the vector further comprises a promoter, a ribosomal binding site, a gene encoding a target protein, and a transcription terminator which are operably linked to each other.

18. The cell of claim 16, wherein the gene encoding the target protein is a *Xanthomonas campestris* (Xc) xanA gene, a *Komagataeibacter xylinus* (Kx) pgm gene, an *Escherichia coli* (EC) galU gene, or a *Xanthomonas campestris* (Xc) ugp gene.

19. A method of producing a target protein in *Komagataeibacter*, the method comprising culturing a *Komagataeibacter* cell comprising a vector of claim 1 in a medium to obtain a culture, wherein the vector further comprises a promoter, a ribosomal binding site, a gene encoding the target protein, and a transcription terminator which are operably linked to each other.

20. The method of claim 19, wherein the target protein is an enzyme involved in cellulose production.

21. A method of evaluating the activity of a promoter in a cell of the genus *Komagataeibacter*, the method comprising:

culturing a first cell of the genus *Komagataeibacter* comprising a first vector of claim 1, wherein the first vector of claim 1 further comprises a candidate promoter, a first reporter gene, and a transcription terminator which are operably linked to each other;

culturing a second cell of the genus *Komagataeibacter* comprising a second vector of claim 1, wherein the second vector of claim 1 comprises a control promoter, a second reporter gene, and a transcription terminator which are operably linked to each other;

and comparing expression of the first and second reporter genes to evaluate the activity of the candidate promoter relative to the control promoter.

\* \* \* \* \*

SEQUENCE LISTING

<160> NUMBER OF SEQ ID NOS: 48

<210> SEQ ID NO 1
<211> LENGTH: 496
<212> TYPE: DNA
<213> ORGANISM: Artificial Sequence
<220> FEATURE:
<223> OTHER INFORMATION: Synthetic pSa origin sequence

<400> SEQUENCE: 1

| | | | | | |
|---|---|---|---|---|---|
| agagggtagt | tatccacgtg | aaaccgctaa | tgccccgcaa | agccttgatt | cacggggctt | 60 |
| tccggcccgc | tccaaaaact | atccacgtga | aatcgctaat | cagggtacgt | gaaatcgcta | 120 |
| atcggagtac | gtgaaatcgc | taataaggtc | acgtgaaatc | gctaatcaaa | aaggcacgtg | 180 |
| agaacgctaa | tagcccttc | agatcaacag | cttgcaaaca | ccctcgctc | cggcaagtag | 240 |
| ttacagcaag | tagtatgttc | aattagcttt | tcaattatga | atatatat | caattattgg | 300 |
| tcgcccttgg | cttgtggaca | atgcgctacg | cgcaccggct | ccgcccgtgg | acaaccgcaa | 360 |
| gcggttgccc | accgtcgagc | gccagcgcct | tgcccacaa | cccggcggcc | ggccgcaaca | 420 |
| gatcgtttta | taaatttttt | tttttgaaaa | agaaaaagcc | cgaaaggcgg | caacctctcg | 480 |
| ggcttctgga | tttccg | | | | | 496 |

<210> SEQ ID NO 2
<211> LENGTH: 666
<212> TYPE: DNA
<213> ORGANISM: Artificial Sequence
<220> FEATURE:
<223> OTHER INFORMATION: Synthetic pSa origin entire sequence

<400> SEQUENCE: 2

| | | | | | |
|---|---|---|---|---|---|
| tttttatccc | cggaagcctg | tggatagagg | gtagttatcc | acgtgaaacc | gctaatgccc | 60 |
| cgcaaagcct | tgattcacgg | ggctttccgg | cccgctccaa | aaactatcca | cgtgaaatcg | 120 |
| ctaatcaggg | tacgtgaaat | cgctaatcgg | agtacgtgaa | atcgctaata | aggtcacgtg | 180 |
| aaatcgctaa | tcaaaaaggc | acgtgagaac | gctaatagcc | ctttcagatc | aacagcttgc | 240 |
| aaacacccct | cgctccggca | agtagttaca | gcaagtagta | tgttcaatta | gcttttcaat | 300 |
| tatgaatata | tatatcaatt | attggtcgcc | cttggcttgt | ggacaatgcg | ctacgcgcac | 360 |
| cggctccgcc | cgtggacaac | cgcaagcggt | tgcccaccgt | cgagcgccag | cgcctttgcc | 420 |
| cacaacccgg | cggccggccg | caacagatcg | ttttataaat | ttttttttt | gaaaagaaa | 480 |
| aagcccgaaa | ggcggcaacc | tctcgggctt | ctggatttcc | gatccccgga | attagagatc | 540 |
| ttggcaggat | atattgtggt | gtaacgttaa | cattaacgtt | tacaatttcg | cgccattcgc | 600 |
| cattcaggct | gcgcaactgt | tgggaagggc | gatcggtgcg | ggcctcttcg | ctattacgcc | 660 |
| agctgg | | | | | | 666 |

<210> SEQ ID NO 3
<211> LENGTH: 668
<212> TYPE: DNA
<213> ORGANISM: Artificial Sequence
<220> FEATURE:
<223> OTHER INFORMATION: Synthetic pUC origin sequence

<400> SEQUENCE: 3

| | | | | | |
|---|---|---|---|---|---|
| tgagcaaaag | gccagcaaaa | ggccaggaac | cgtaaaaagg | ccgcgttgct | ggcgtttttc | 60 |
| cataggctcc | gccccctga | cgagcatcac | aaaaatcgac | gctcaagtca | gaggtggcga | 120 |
| aacccgacag | gactataaag | ataccaggcg | tttccccctg | gaagctccct | cgtgcgctct | 180 |

```
cctgttccga ccctgccgct taccggatac ctgtccgcct ttctcccttc gggaagcgtg    240
gcgctttctc atagctcacg ctgtaggtat ctcagttcgg tgtaggtcgt tcgctccaag    300
ctgggctgtg tgcacgaacc ccccgttcag cccgaccgct gcgccttatc cggtaactat    360
cgtcttgagt ccaacccggt aagacacgac ttatcgccac tggcagcagc cactggtaac    420
aggattagca gagcgaggta tgtaggcggt gctacagagt tcttgaagtg gtggcctaac    480
tacggctaca ctagaagaac agcatttggt atctgcgctc tgctgaagcc agttaccttc    540 ggaaaagag ttggtagctc ttgatccggc aaacaaacca ccgctggtag cggtggtttt    600
tttgtttgca agcagcagat tacgcgcaga aaaaaggat ctcaagaaga tcctttgatc    660
tttctac                                                              668
```

<210> SEQ ID NO 4
<211> LENGTH: 1191
<212> TYPE: DNA
<213> ORGANISM: Artificial Sequence
<220> FEATURE:
<223> OTHER INFORMATION: Synthetic tetracycline resistant gene
<400> SEQUENCE: 4

```
atgaaatcta acaatgcgct catcgtcatc ctcggcaccg tcaccctgga tgctgtaggc     60
ataggcttgg ttatgccggt actgccgggc ctcttgcggg atatcgtcca ttccgacagc    120
atcgccagtc actatggcgt gctgctagcg ctatatgcgt tgatgcaatt tctatgcgca    180
cccgttctcg gagcactgtc cgaccgcttt ggccgccgcc cagtcctgct cgcttcgcta    240
cttggagcca ctatcgacta cgcgatcatg gcgaccacac ccgtcctgtg gatcctctac    300 gccgacgca tcgtggccgg catcaccggc gccacaggtg cggttgctgg cgcctatatc    360
gccgacatca ccgatgggga agatcgggct cgccacttcg gctcatgagc gcttgtttc     420 ggcgtgggta tggtggcagg ccccgtggcc gggggactgt tgggcgccat ctccttgcat    480
gcaccattcc ttgcggcggc ggtgctcaac ggcctcaacc tactactggg ctgcttccta    540
atgcaggagt cgcataaggg agagcgtcga ccgatgccct tgagagcctt caacccagtc    600
agctccttcc ggtgggcgcg gggcatgact atcgtcgccg cacttatgac tgtcttcttt    660
atcatgcaac tcgtaggaca ggtgccggca gcgctctggg tcattttcgg cgaggaccgc    720
tttcgctgga gcgcgacgat gatcggcctg tcgcttgcgg tattcggaat cttgcacgcc    780
ctcgctcaag ccttcgtcac tggtcccgcc accaaacgtt tcggcgagaa gcaggccatt    840
atcgccggca tggcggccga cgcgctgggc tacgtcttgc tggcgttcgc gacgcgaggc    900
tggatggcct tccccattat gattcttctc gcttccggcg gcatcgggat gcccgcgttg    960
caggccatgc tgtccaggca ggtagatgac gaccatcagg gacagcttca aggatcgctc   1020
gcggctctta ccagcctaac ttcgatcact ggaccgctga tcgtcacggc gatttatgcc   1080
gcctcggcga gcacatggaa cgggttggca tggattgtag gcgccgccct ataccttgtc   1140
tgcctccccg cgttgcgtcg cggtgcatgg agccgggcca cctcgacctg a            1191
```

<210> SEQ ID NO 5
<211> LENGTH: 35
<212> TYPE: DNA
<213> ORGANISM: Artificial Sequence
<220> FEATURE:
<223> OTHER INFORMATION: Synthetic tac promoter
<400> SEQUENCE: 5

```
gagctgttga caattaatca tcggctcgta taatg                         35

<210> SEQ ID NO 6
<211> LENGTH: 538
<212> TYPE: DNA
<213> ORGANISM: Artificial Sequence
<220> FEATURE:
<223> OTHER INFORMATION: Synthetic gapA promoter

<400> SEQUENCE: 6
aacttcggcg gcgcccgagc gtgaacagca cgggctgacc aacctgtgcg cgcggggcgg    60
ttacgtgctg gccgaagccg aaggcgcgcg acaggtcacg ctgatcgcca cgggacatga   120
ggccatactg gcactggcgg cgcgcaaact gctgcgggac gcggggggttg cggcggctgt   180 cgtctccctt ccatgctggg aactgttcgc cgtgcaaaaa atgacgtatc gtgccgccgt   240
gctgggaacg gcaccccgga tcgggatcga ggccgcttca gggtttggat gggaacgatg   300
gcttggaaca gcgggctgt ttgtcggtat tgacggattc ggggcgtctt acgccccga    360 ccggccagac agccctgccg gcatcacgcc ggaacggatc tgccacgacg cattgcggct   420
ggtccgcccc catgccgacg ccctggttga accgcggga ggaaacggcg cgccgcccgg    480
gatggcatcg gtcgatgcca gtgtgtgaaa tgtcagacct tacgagaaaa ataagaaa     538

<210> SEQ ID NO 7
<211> LENGTH: 29
<212> TYPE: DNA
<213> ORGANISM: Artificial Sequence
<220> FEATURE:
<223> OTHER INFORMATION: Synthetic Bla promoter

<400> SEQUENCE: 7
ttcaaatatg tatccgctca tgagacaat                                29

<210> SEQ ID NO 8
<211> LENGTH: 13
<212> TYPE: DNA
<213> ORGANISM: Artificial Sequence
<220> FEATURE:
<223> OTHER INFORMATION: Synthetic RBS sequence

<400> SEQUENCE: 8
ggacgagcta ttg                                                 13

<210> SEQ ID NO 9
<211> LENGTH: 70
<212> TYPE: DNA
<213> ORGANISM: Artificial Sequence
<220> FEATURE:
<223> OTHER INFORMATION: Synthetic Mulicloning site

<400> SEQUENCE: 9
gattgggtac cgagctcgaa ttcgtacccg gggatcctct agagtcgacc tgcaggcatg    60
caagcttggc                                                     70

<210> SEQ ID NO 10
<211> LENGTH: 326
<212> TYPE: DNA
<213> ORGANISM: Artificial Sequence
<220> FEATURE:
<223> OTHER INFORMATION: Synthetic terminator sequence

<400> SEQUENCE: 10
tgcctggcgg cagtagcgcg gtggtcccac ctgaccccat gccgaactca gaagtgaaac    60
```

```
gccgtagcgc cgatggtagt gtggggtctc cccatgcgag agtagggaac tgccaggcat    120
caaataaaac gaaaggctca gtcgaaagac tgggcctttc gttttatctg ttgtttgtcg    180
gtgaacgctc tcctgagtag gacaaatccg ccgggagcgg atttgaacgt tgcgaagcaa    240
cggcccggag ggtggcgggc aggacgcccg ccataaactg ccaggcatca aattaagcag    300
aaggccatcc tgacggatgg ccttt                                          326
```

<210> SEQ ID NO 11
<211> LENGTH: 2795
<212> TYPE: DNA
<213> ORGANISM: Artificial Sequence
<220> FEATURE:
<223> OTHER INFORMATION: Synthetic pTSa vector

<400> SEQUENCE: 11

```
gaattcagcc agcaagacag cgatagaggg tagttatcca cgtgaaaccg ctaatgcccc     60
gcaaagcctt gattcacggg gctttccggc ccgctccaaa aactatccac gtgaaatcgc    120
taatcagggt acgtgaaatc gctaatcgga gtacgtgaaa tcgctaataa ggtcacgtga    180
aatcgctaat caaaaaggca cgtgagaacg ctaatagccc tttcagatca acagcttgca    240
aacacccctc gctccggcaa gtagttacag caagtagtat gttcaattag cttttcaatt    300
atgaatatat atcaatta ttggtcgccc ttggcttgtg gacaatgcgc tacgcgcacc     360
ggctccgccc gtggacaacc gcaagcggtt gcccaccgtc gagcgccagc gcctttgccc    420
acaacccggc ggccggccgc aacagatcgt tttataaatt tttttttttg aaaaagaaaa    480
agcccgaaag gcggcaacct ctcgggcttc tggatttccg atcacctgta agtcggacga    540
attcggcgct cttccgcttc ctcgctcact gactcgctgc gctcggtcgt tcggctgcgg    600
cgagcggtat cagctcactc aaaggcggta atacggttat ccacagaatc aggggataac    660
gcaggaaaga acatgtgagc aaaaggccag caaaaggcca ggaaccgtaa aaaggccgcg    720
ttgctggcgt ttttccatag gctccgcccc cctgacgagc atcacaaaaa tcgacgctca    780
agtcagaggt ggcgaaaccc gacaggacta taaagatacc aggcgtttcc ccctggaagc    840
tccctcgtgc gctctcctgt tccgaccctg ccgcttaccg gatacctgtc gcctttctc    900 ccttcgggaa gcgtggcgct ttctcatagc tcacgctgta ggtatctcag ttcggtgtag    960
gtcgttcgct ccaagctggg ctgtgtgcac gaaccccccg ttcagcccga ccgctgcgcc   1020
ttatccggta actatcgtct tgagtccaac ccggtaagac acgacttatc gccactggca   1080
gcagccactg gtaacaggat tagcagagcg aggtatgtag cggtgctac agagttcttg   1140 aagtggtggc ctaactacgg ctacactaga agaacagcat ttggtatctg cgctctgctg   1200
aagccagtta ccttcggaaa aagagttggt agctcttgat ccggcaaaca aaccaccgct   1260
ggtagcggtg gtttttttgt ttgcaagcag cagattacgc gcagaaaaaa aggatctcaa   1320
gaagatcctt tgatcttttc tacggggtct gacgctcagt ggaacgaaaa ctcacgttaa   1380
ttctcatgtt tgacagctta tcatcgataa gctttaatgc ggtagtttat cacagttaaa   1440
ttgctaacgc agtcaggcac cgtgtatgaa atctaacaat gcgctcatcg tcatcctcgg   1500
caccgtcacc ctggatgctg taggcatagg cttggttatg ccgtactgc cgggcctctt   1560 gcgggatatc gtccattccg acagcatcgc cagtcactat ggcgtgctgc tagcgctata   1620
tgcgttgatg caatttctat gcgcacccgt tctcggagca ctgtccgacc gctttggccg   1680
ccgcccagtc ctgctcgctt cgctacttgg agccactatc gactacgcga tcatggcgac   1740
```

```
cacacccgtc ctgtggatcc tctacgccgg acgcatcgtg gccggcatca ccggcgccac    1800
aggtgcggtt gctggcgcct atatcgccga catcaccgat ggggaagatc gggctcgcca    1860
cttcgggctc atgagcgctt gtttcggcgt gggtatggtg gcaggccccg tggccggggg    1920
actgttgggc gccatctcct tgcatgcacc attccttgcg gcggcggtgc tcaacggcct    1980
caacctacta ctgggctgct tcctaatgca ggagtcgcat aagggagagc gtcgaccgat    2040
gcccttgaga gccttcaacc cagtcagctc cttccggtgg gcgcggggca tgactatcgt    2100
cgccgcactt atgactgtct tctttatcat gcaactcgta ggacaggtgc cggcagcgct    2160
ctgggtcatt ttcggcgagg accgctttcg ctggagcgcg acgatgatcg gcctgtcgct    2220
tgcggtattc ggaatcttgc acgccctcgc tcaagccttc gtcactggtc ccgccaccaa    2280
acgtttcggc gagaagcagg ccattatcgc cggcatggcg gccgacgcgc tgggctacgt    2340
cttgctggcg ttcgcgacgc gaggctggat ggccttcccc attatgattc ttctcgcttc    2400
cggcggcatc gggatgcccg cgttgcaggc catgctgtcc aggcaggtag atgacgacca    2460
tcagggacag cttcaaggat cgctcgcggc tcttaccagc ctaacttcga tcactggacc    2520
gctgatcgtc acggcgattt atgccgcctc ggcgagcaca tggaacgggt tggcatggat    2580
tgtaggcgcc gccctatacc ttgtctgcct ccccgcgttg cgtcgcggtg catggagccg    2640
ggccacctcg acctgaatgg aagccggcgg cacctcgcta acggattcac cactccaaga    2700
attggagcca atttttaagg cagttattgg tgcccttaaa cgcctggttg ctacgcctga    2760
ataagtgata taagcggat gaatggcaga aattc                                2795

<210> SEQ ID NO 12
<211> LENGTH: 3576
<212> TYPE: DNA
<213> ORGANISM: Artificial Sequence
<220> FEATURE:
<223> OTHER INFORMATION: Synthetic pTSa-EX1 vector

<400> SEQUENCE: 12
gaattcagcc agcaagacag cgatagaggg tagttatcca cgtgaaaccg ctaatgcccc      60
gcaaagcctt gattcacggg gctttccggc ccgctccaaa aactatccac gtgaaatcgc     120 taatcaggt acgtgaaatc gctaatcgga gtacgtgaaa tcgctaataa ggtcacgtga     180
aatcgctaat caaaaaggca cgtgagaacg ctaatagccc tttcagatca acagcttgca     240 aacaccctc gctccggcaa gtagttacag caagtagtat gttcaattag cttttcaatt     300
atgaatatat atcaattta ttggtcgccc ttggcttgtg gacaatgcgc tacgcgcacc     360
ggctccgccc gtggacaacc gcaagcggtt gccaccgtc gagcgccagc gcctttgccc      420
acaacccggc ggccggccgc aacagatcgt tttataaatt ttttttttg aaaaagaaaa     480 agcccgaaag gcggcaacct ctcgggcttc tggatttccg atcacctgta agtcggacgt     540
tccgatcacc tgtaacgatg cgtccggcgt agaggatccg gagcttatcg actgcacggt     600
gcaccaatgc ttctggcgtc aggcagccat cggaagctgt ggtatggctg tgcaggtcgt     660
aaatcactgc ataattcgtg tcgctcaagg cgcactcccg ttctggataa tgttttttgc     720
gccgacatca taacgttct ggcaaatatt ctgaaatgag ctgttgacaa ttaatcatcg     780
gctcgtataa tgtgtggaat tgtgagcgga taacaatttc acacagggac gagctattga     840
ttgggtaccg agctcgaatt cgtacccggg gatcctctag agtcgacctg caggcatgca     900
agcttggctg ttttggcgga tgagagaaga ttttcagcct gatacagatt aaatcagaac     960
gcagaagcgg tctgataaaa cagaatttgc ctggcggcag tagcgcggtg gtcccacctg    1020
```

```
acccaatgcc gaactcagaa gtgaaacgcc gtagcgccga tggtagtgtg gggtctcccc    1080
atgcgagagt agggaactgc caggcatcaa ataaaacgaa aggctcagtc gaaagactgg    1140
gcctttcgtt ttatctgttg tttgtcggtg aacgctctcc tgagtaggac aaatccgccg    1200
ggagcggatt tgaacgttgc gaagcaacgg cccggagggt ggcgggcagg acgcccgcca    1260
taaactgcca ggcatcaaat taagcagaag gccatcctga cggatggcct ttttgcaaga    1320
acatgtgagc acttccgctt cctcgctcac tgactcgctg cgctcggtcg ttcggctgcg    1380
gcgagcggta tcagctcact caaaggcggt aatacggtta tccacagaat caggggataa    1440
cgcaggaaag aacatgtgag caaaaggcca gcaaaaggcc aggaaccgta aaaaggccgc    1500
gttgctggcg ttttttccata ggctccgccc ccctgacgag catcacaaaa atcgacgctc    1560
aagtcagagg tggcgaaacc cgacaggact ataaagatac caggcgtttc ccctggaag    1620
ctccctcgtg cgctctcctg ttccgaccct gccgcttacc ggatacctgt ccgcctttct    1680
cccttcggga agcgtggcgc tttctcatag ctcacgctgt aggtatctca gttcggtgta    1740
ggtcgttcgc tccaagctgg gctgtgtgca cgaaccccc gttcagcccg accgctgcgc    1800
cttatccggt aactatcgtc ttgagtccaa cccggtaaga cacgacttat cgccactggc    1860
agcagccact ggtaacagga ttagcagagc gaggtatgta ggcggtgcta cagagttctt    1920
gaagtggtgg cctaactacg gctacactag aagaacagca tttggtatct gcgctctgct    1980
gaagccagtt accttcggaa aaagagttgg tagctcttga tccggcaaac aaaccaccgc    2040
tggtagcggt ggtttttttg tttgcaagca gcagattacg cgcagaaaaa aaggatctca    2100
agaagatcct ttgatctttt ctacgggggtc tgacgctcag tggaacgaaa actcacgtta    2160
attctcatgt ttgacagctt atcatcgata agctttaatg cggtagttta tcacagttaa    2220
attgctaacg cagtcaggca ccgtgtatga aatctaacaa tgcgctcatc gtcatcctcg    2280
gcaccgtcac cctggatgct gtaggcatag gcttggttat gccggtactg ccgggcctct    2340
tgcgggatat cgtccattcc gacagcatcg ccagtcacta tggcgtgctg ctagcgctat    2400
atgcgttgat gcaatttcta tgcgcacccg ttctcggagc actgtccgac cgctttggcc    2460
gccgcccagt cctgctcgct tcgctacttg gagccactat cgactacgcg atcatggcga    2520
ccacacccgt cctgtggatc ctctacgccg gacgcatcgt ggccggcatc accggcgcca    2580
caggtgcggt tgctggcgcc tatatcgccg acatcaccga tggggaagat cgggctcgcc    2640
acttcgggct catgagcgct tgtttcggcg tgggtatggt ggcaggcccc gtggccgggg    2700
gactgttggg cgccatctcc ttgcatgcac cattccttgc ggcggcggtg ctcaacggcc    2760
tcaacctact actgggctgc ttcctaatgc aggagtcgca taagggagag cgtcgaccga    2820
tgcccttgag agccttcaac ccagtcagct ccttccggtg ggcgcgggc atgactatcg    2880
tcgccgcact tatgactgtc ttctttatca tgcaactcgt aggacaggtg ccggcagcgc    2940
tctgggtcat tttcggcgag gaccgctttc gctggagcgc gacgatgatc ggcctgtcgc    3000
ttgcggtatt cggaatcttg cacgccctcg ctcaagcctt cgtcactggt cccgccacca    3060
aacgtttcgg cgagaagcag gccattatcg ccggcatggc ggccgacgcg ctgggctacg    3120
tcttgctggc gttcgcgacg cgaggctgga tggccttccc cattatgatt cttctcgctt    3180
ccggcggcat cgggatgccc gcgttgcagg ccatgctgtc caggcaggta gatgacgacc    3240
atcagggaca gcttcaagga tcgctcgcgg ctcttaccag cctaacttcg atcactggac    3300
cgctgatcgt cacggcgatt tatgccgcct cggcgagcac atggaacggg ttggcatgga    3360
```

| | |
|---|---|
| ttgtaggcgc cgccctatac cttgtctgcc tccccgcgtt gcgtcgcggt gcatggagcc | 3420 |
| gggccacctc gacctgaatg gaagccggcg gcacctcgct aacggattca ccactccaag | 3480 |
| aattggagcc aattttttaag gcagttattg gtgcccttaa acgcctggtt gctacgcctg | 3540 |
| aataagtgat aataagcgga tgaatggcag aaattc | 3576 |

```
<210> SEQ ID NO 13
<211> LENGTH: 3810
<212> TYPE: DNA
<213> ORGANISM: Artificial Sequence
<220> FEATURE:
<223> OTHER INFORMATION: Synthetic pTSa-EX2 vector

<400> SEQUENCE: 13
```

| | |
|---|---|
| gaattcagcc agcaagacag cgatagaggg tagttatcca cgtgaaaccg ctaatgcccc | 60 |
| gcaaagcctt gattcacggg gctttccggc ccgctccaaa aactatccac gtgaaatcgc | 120 |
| taatcagggt acgtgaaatc gctaatcgga gtacgtgaaa tcgctaataa ggtcacgtga | 180 |
| aatcgctaat caaaaaggca cgtgagaacg ctaatagccc tttcagatca acagcttgca | 240 |
| aacacccctc gctccggcaa gtagttacag caagtagtat gttcaattag ctttttcaatt | 300 |
| atgaatatat atatcaatta ttggtcgccc ttggcttgtg gacaatgcgc tacgcgcacc | 360 |
| ggctccgccc gtggacaacc gcaagcggtt gcccaccgtc gagcgccagc gcctttgccc | 420 |
| acaacccggc ggccggccgc aacagatcgt tttataaatt ttttttttttg aaaaagaaaa | 480 |
| agcccgaaag gcggcaacct ctcgggcttc tggatttccg atcacctgta agtcggacga | 540 |
| acttcggcgg cgcccgagcg tgaacagcac gggctgacca acctgtgcgc gcggggcggt | 600 |
| tacgtgctgg ccgaagccga aggcgcgcga caggtcacgc tgatcgccac gggacatgag | 660 |
| gccatactgg cactggcggc gcgcaaactg ctgcgggacg cggggggttgc ggcggctgtc | 720 |
| gtctcccttc catgctggga actgttcgcc gtgcaaaaaa tgacgtatcg tgccgccgtg | 780 |
| ctgggaacgg caccccggat cgggatcgag gccgcttcag ggtttggatg gaacgatgg | 840 |
| cttggaacag gcgggctgtt tgtcggtatt gacggattcg gggcgtctta cgcccccgac | 900 |
| cggccagaca gccctgccgg catcacgccg gaacggatct gccacgacgc attgcggctg | 960 |
| gtccgcccccc atgccgacgc cctggttgaa accgcgggag gaaacggcgc gccgcccggg | 1020 |
| atggcatcgg tcgatgccag tgtgtgaaat gtcagacctt acggagaaaa taagaaaagg | 1080 |
| acgagctatt gattcgtacc cggggatcct ctagagtcga cctgcaggca tgcaagcttg | 1140 |
| gctgttttgg cggatgagag aagattttca gcctgataca gattaaatca gaacgcagaa | 1200 |
| gcggtctgat aaaacagaat tgcctggcg gcagtagcgc ggtggtccca cctgacccca | 1260 |
| tgccgaactc agaagtgaaa cgccgtagcc ccgatggtag tgtggggtct ccccatgcga | 1320 |
| gagtagggaa ctgccaggca tcaaataaaa cgaaaggctc agtcgaaaga ctgggccttt | 1380 |
| cgttttatct gttgtttgtc ggtgaacgct ctcctgagta ggacaaatcc gccgggagcg | 1440 |
| gatttgaacg ttgcgaagca acggcccgga gggtggcggg caggacgccc gccataaact | 1500 |
| gccaggcatc aaattaagca gaaggccatc ctgacggatg cctttttgc aagaacatgt | 1560 |
| gagcacttcc gcttcctcgc tcactgactc gctgcgctcg tcgttcggc tgcggcgagc | 1620 |
| ggtatcagct cactcaaagg cggtaatacg gttatccaca gaatcagggg ataacgcagg | 1680 |
| aaagaacatg tgagcaaaag gccagcaaaa ggccaggaac cgtaaaaagg ccgcgttgct | 1740 |
| ggcgtttttc cataggctcc gcccccctga cgagcatcac aaaaatcgac gctcaagtca | 1800 |
| gaggtggcga aacccgacag gactataaag ataccaggcg tttccccctg gaagctccct | 1860 |

```
cgtgcgctct cctgttccga ccctgccgct taccggatac ctgtccgcct ttctcccttc    1920
gggaagcgtg gcgctttctc atagctcacg ctgtaggtat ctcagttcgg tgtaggtcgt    1980
tcgctccaag ctgggctgtg tgcacgaacc ccccgttcag cccgaccgct gcgccttatc    2040
cggtaactat cgtcttgagt ccaacccggt aagacacgac ttatcgccac tggcagcagc    2100
cactggtaac aggattagca gagcgaggta tgtaggcggt gctacagagt tcttgaagtg    2160
gtggcctaac tacggctaca ctagaagaac agcatttggt atctgcgctc tgctgaagcc    2220
agttaccttc ggaaaaagag ttggtagctc ttgatccggc aaacaaacca ccgctggtag    2280
cggtggtttt tttgtttgca agcagcagat tacgcgcaga aaaaaaggat ctcaagaaga    2340
tcctttgatc ttttctacgg ggtctgacgc tcagtggaac gaaaactcac gttaattctc    2400
atgtttgaca gcttatcatc gataagcttt aatgcggtag tttatcacag ttaaattgct    2460
aacgcagtca ggcaccgtgt atgaaatcta acaatgcgct catcgtcatc ctcggcaccg    2520
tcaccctgga tgctgtaggc ataggcttgg ttatgccggt actgccgggc ctcttgcggg    2580
atatcgtcca ttccgacagc atcgccagtc actatggcgt gctgctagcg ctatatgcgt    2640
tgatgcaatt tctatgcgca cccgttctcg gagcactgtc cgaccgcttt ggccgccgcc    2700
cagtcctgct cgcttcgcta cttggagcca ctatcgacta cgcgatcatg gcgaccacac    2760
ccgtcctgtg gatcctctac gccggacgca tcgtggccgg catcaccggc gccacaggtg    2820
cggttgctgg cgcctatatc gccgacatca ccgatgggga agatcgggct cgccacttcg    2880
ggctcatgag cgcttgtttc ggcgtgggta tggtggcagg ccccgtggcc ggggactgt    2940 tgggcgccat ctccttgcat gcaccattcc ttgcggcggc ggtgctcaac ggcctcaacc    3000
tactactggg ctgcttccta atgcaggagt cgcataaggg agagcgtcga ccgatgccct    3060
tgagagcctt caacccagtc agctccttcc ggtgggcgcg gggcatgact atcgtcgccg    3120
cacttatgac tgtcttcttt atcatgcaac tcgtaggaca ggtgccggca gcgctctggg    3180
tcattttcgg cgaggaccgc tttcgctgga gcgcgacgat gatcggcctg tcgcttgcgg    3240
tattcggaat cttgcacgcc ctcgctcaag ccttcgtcac tggtcccgcc accaaacgtt    3300
tcggcgagaa gcaggccatt atcgccggca tggcggccga cgcgctgggc tacgtcttgc    3360
tggcgttcgc gacgcgaggc tggatggcct tccccattat gattcttctc gcttccggcg    3420
gcatcgggat gcccgcgttg caggccatgc tgtccaggca ggtagatgac gaccatcagg    3480
gacagcttca aggatcgctc gcggctctta ccagcctaac ttcgatcact ggaccgctga    3540
tcgtcacggc gatttatgcc gcctcggcga gcacatggaa cgggttggca tggattgtag    3600
gcgccgccct ataccttgtc tgcctccccg cgttgcgtcg cggtgcatgg agccgggcca    3660
cctcgacctg aatggaagcc ggcggcacct cgctaacgga ttcaccactc caagaattgg    3720
agccaatttt taaggcagtt attggtgccc ttaaacgcct ggttgctacg cctgaataag    3780
tgataataag cggatgaatg gcagaaattc                                     3810
```

<210> SEQ ID NO 14
<211> LENGTH: 3539
<212> TYPE: DNA
<213> ORGANISM: Artificial Sequence
<220> FEATURE:
<223> OTHER INFORMATION: Synthetic pTSa-EX3 vector

<400> SEQUENCE: 14

```
gaattcagcc agcaagacag cgatagaggg tagttatcca cgtgaaaccg ctaatgcccc      60
```

```
gcaaagcctt gattcacggg gctttccggc ccgctccaaa aactatccac gtgaaatcgc    120
taatcagggt acgtgaaatc gctaatcgga gtacgtgaaa tcgctaataa ggtcacgtga    180
aatcgctaat caaaaaggca cgtgagaacg ctaatagccc tttcagatca acagcttgca    240
aacacccctc gctccggcaa gtagttacag caagtagtat gttcaattag cttttcaatt    300
atgaatatat atatcaatta ttggtcgccc ttggcttgtg gacaatgcgc tacgcgcacc    360
ggctccgccc gtggacaacc gcaagcggtt gcccaccgtc gagcgccagc gcctttgccc    420
acaacccggc ggccggccgc aacagatcgt tttataaatt ttttttttg aaaagaaaa      480 agcccgaaag gcggcaacct ctcgggcttc tggatttccg atcacctgta agtcggacgc    540
gatgcgtccg gcgtagagga tccggagctt atcgactgca cggtgcacca atgcttctgg    600
cgtcaggcag ccatcggaag ctgtggtatg gctgtgcagg tcgtaaatca ctgcataatt    660
cgtgtcgctc aaggcgcact cccgttctgg ataatgtttt ttgcgccgac atcataacgg    720
ttctggcaaa tattctgaaa tttcaaatat gtatccgctc atgagacaat tgtggaattg    780
tgagcggata acaatttcac acaggacgga gctattgatt gggtaccgag ctcgaattcg    840
tacccgggga tcctctagag tcgacctgca ggcatgcaag cttggctgtt ttggcggatg    900
agagaagatt ttcagcctga tacagattaa atcagaacgc agaagcggtc tgataaaaca    960
gaatttgcct ggcggcagta gcgcggtggt cccacctgac cccatgccga actcagaagt   1020
gaaacgccgt agcgccgatg gtagtgtggg gtctccccat gcgagagtag ggaactgcca   1080
ggcatcaaat aaaacgaaag gctcagtcga agactgggcc ctttcgtttt atctgttgtt   1140
tgtcggtgaa cgctctcctg agtaggacaa atccgccggg agcggatttg aacgttgcga   1200
agcaacggcc cggagggtgg cgggcaggac gcccgccata aactgccagg catcaaatta   1260
agcagaaggc catcctgacg gatggccttt ttgccttccg cttcctcgct cactgactcg   1320
ctgcgctcgg tcgttcggct gcggcgagcg gtatcagctc actcaaaggc ggtaatacgg   1380
ttatccacag aatcagggga taacgcagga aagaacatgt gagcaaaagg ccagcaaaag   1440
gccaggaacc gtaaaaaggc cgcgttgctg gcgtttttcc ataggctccg ccccctgac    1500 gagcatcaca aaaatcgacg ctcaagtcag aggtggcgaa acccgacagg actataaaga   1560
taccaggcgt ttccccctgg aagctccctc gtgcgctctc ctgttccgac cctgccgctt   1620
accggatacc tgtccgcctt tctcccttcg ggaagcgtgg cgctttctca tagctcacgc   1680
tgtaggtatc tcagttcggt gtaggtcgtt cgctccaagc tgggctgtgt gcacgaaccc   1740
cccgttcagc ccgaccgctg cgccttatcc ggtaactatc gtcttgagtc aacccggta    1800 agacacgact tatcgccact ggcagcagcc actggtaaca ggattagcag agcgaggtat   1860
gtaggcggtg ctacagagtt cttgaagtgg tggcctaact acggctacac tagaagaaca   1920
gcatttggta tctgcgctct gctgaagcca gttaccttcg gaaaagagt tggtagctct    1980 tgatccggca acaaaccac cgctggtagc ggtggttttt ttgtttgcaa gcagcagatt    2040
acgcgcagaa aaaaggatc tcaagaagat cctttgatct tttctacggg gtctgacgct    2100
cagtggaacg aaaactcacg ttaattctca tgtttgacag cttatcatcg ataagcttta   2160
atgcggtagt ttatcacagt taaattgcta acgcagtcag gcaccgtgta tgaaatctaa   2220
caatgcgctc atcgtcatcc tcggcaccgt caccctggat gctgtaggca taggcttggt   2280
tatgccggta ctgccgggcc tcttgcggga tatcgtccat tccgacagca tcgccagtca   2340
ctatggcgtg ctgctagcgc tatatgcgtt gatgcaattt ctatgcgcac ccgttctcgg   2400
agcactgtcc gaccgctttg gccgccgccc agtcctgctc gcttcgctac ttggagccac   2460
```

-continued

| | |
|---|---|
| tatcgactac gcgatcatgg cgaccacacc cgtcctgtgg atcctctacg ccggacgcat | 2520 |
| cgtggccggc atcaccggcg ccacaggtgc ggttgctggc gcctatatcg ccgacatcac | 2580 |
| cgatggggaa gatcgggctc gccacttcgg gctcatgagc gcttgtttcg gcgtgggtat | 2640 |
| ggtggcaggc cccgtggccg ggggactgtt gggcgccatc tccttgcatg caccattcct | 2700 |
| tgcggcggcg gtgctcaacg gcctcaacct actactgggc tgcttcctaa tgcaggagtc | 2760 |
| gcataaggga gagcgtcgac cgatgccctt gagagccttc aacccagtca gctccttccg | 2820 |
| gtgggcgcgg ggcatgacta tcgtcgccgc acttatgact gtcttcttta tcatgcaact | 2880 |
| cgtaggacag gtgccggcag cgctctgggt cattttcggc gaggaccgct ttcgctggag | 2940 |
| cgcgacgatg atcggcctgt cgcttgcggt attcggaatc ttgcacgccc tcgctcaagc | 3000 |
| cttcgtcact ggtcccgcca ccaaacgttt cggcgagaag caggccatta tcgccggcat | 3060 |
| ggcggccgac gcgctgggct acgtcttgct ggcgttcgcg acgcgaggct ggatggcctt | 3120 |
| ccccattatg attcttctcg cttccggcgg catcgggatg cccgcgttgc aggccatgct | 3180 |
| gtccaggcag gtagatgacg accatcaggg acagcttcaa ggatcgctcg cggctcttac | 3240 |
| cagcctaact tcgatcactg gaccgctgat cgtcacggcg atttatgccg cctcggcgag | 3300 |
| cacatggaac gggttggcat ggattgtagg cgccgcccta taccttgtct gcctccccgc | 3360 |
| gttgcgtcgc ggtgcatgga gccgggccac ctcgacctga atggaagccg gcggcacctc | 3420 |
| gctaacggat tcaccactcc aagaattgga gccaattttt aaggcagtta ttggtgccct | 3480 |
| taaacgcctg gttgctacgc ctgaataagt gataataagc ggatgaatgg cagaaattc | 3539 |

<210> SEQ ID NO 15
<211> LENGTH: 4843
<212> TYPE: DNA
<213> ORGANISM: Artificial Sequence
<220> FEATURE:
<223> OTHER INFORMATION: Synthetic pTSaP vector sequence

<400> SEQUENCE: 15

| | |
|---|---|
| aagaacatgt gagcaaaagg ccagcaaaag gccaggaacc gtaaaaaggc cgcgttgctg | 60 |
| gcgtttttcc ataggctccg cccccctgac gagcatcaca aaaatcgacg ctcaagtcag | 120 |
| aggtggcgaa acccgacagg actataaaga taccaggcgt ttccccctgg aagctccctc | 180 |
| gtgcgctctc ctgttccgac cctgccgctt accggatacc tgtccgcctt tctcccttcg | 240 |
| ggaagcgtgg cgctttctca tagctcacgc tgtaggtatc tcagttcggt gtaggtcgtt | 300 |
| cgctccaagc tgggctgtgt gcacgaaccc cccgttcagc ccgaccgctg cgccttatcc | 360 |
| ggtaactatc gtcttgagtc caacccggta agacacgact tatcgccact ggcagcagcc | 420 |
| actggtaaca ggattagcag agcgaggtat gtaggcggtg ctacagagtt cttgaagtgg | 480 |
| tggcctaact acggctacac tagaagaaca gcatttggta tctgcgctct gctgaagcca | 540 |
| gttaccttcg gaaaaagagt tggtagctct tgatccggca acaaaccac cgctggtagc | 600 |
| ggtggttttt ttgtttgcaa gcagcagatt acgcgcagaa aaaaaggatc tcaagaagat | 660 |
| cctttgatct tttctacggg gtctgacgct cagtggaacg aaaactcacg ttaattctca | 720 |
| tgtttgacag cttatcatcg ataagcttta atgcggtagt ttatcacagt taaattgcta | 780 |
| acgcagtcag gcaccgtgta tgaaatctaa caatgcgctc atcgtcatcc tcggcaccgt | 840 |
| caccctggat gctgtaggca taggcttggt tatgccggta ctgccgggcc tcttgcggga | 900 |
| tatcgtccat tccgacagca tcgccagtca ctatggcgtg ctgctagcgc tatatgcgtt | 960 |

```
gatgcaattt ctatgcgcac ccgttctcgg agcactgtcc gaccgctttg ccgccgccc      1020 agtcctgctc gcttcgctac ttggagccac tatcgactac gcgatcatgg cgaccacacc     1080
cgtcctgtgg atcctctacg ccggacgcat cgtggccggc atcaccggcg ccacaggtgc     1140
ggttgctggc gcctatatcg ccgacatcac cgatggggaa gatcgggctc gccacttcgg     1200
gctcatgagc gcttgtttcg gcgtgggtat ggtggcaggc cccgtggccg ggggactgtt     1260
gggcgccatc tccttgcatg caccattcct tgcggcggcg gtgctcaacg gcctcaacct     1320
actactgggc tgcttcctaa tgcaggagtc gcataaggga gagcgtcgac cgatgccctt     1380
gagagccttc aacccagtca gctccttccg gtgggcgcgg ggcatgacta tcgtcgccgc     1440
acttatgact gtcttcttta tcatgcaact cgtaggacag gtgccggcag cgctctgggt     1500
cattttcggc gaggaccgct ttcgctggag cgcgacgatg atcggcctgt cgcttgcggt     1560
attcggaatc ttgcacgccc tcgctcaagc cttcgtcact ggtcccgcca ccaaacgttt     1620
cggcgagaag caggccatta tcgccggcat ggcggccgac gcgctgggct acgtcttgct     1680
ggcgttcgcg acgcgaggct ggatggcctt ccccattatg attcttctcg cttccggcgg     1740
catcgggatg cccgcgttgc aggccatgct gtccaggcag gtagatgacg accatcaggg     1800
acagcttcaa ggatcgctcg cggctcttac cagcctaact tcgatcactg gaccgctgat     1860
cgtcacggcg atttatgccg cctcggcgag cacatggaac gggttggcat ggattgtagg     1920
cgccgcccta taccttgtct gcctccccgc gttgcgtcgc ggtgcatgga gccgggccac     1980
ctcgacctga atggaagccg gcggcacctc gctaacggat tcaccactcc aagaattgga     2040
gccaattttt aaggcagtta ttggtgccct taaacgcctg gttgctacgc ctgaataagt     2100
gataataagc ggatgaatgg cagaaattcg aattcagcca gcaagacagc gatagagggt     2160
agttatccac gtgaaaccgc taatgccccg caaagccttg attcacgggg ctttccggcc     2220
cgctccaaaa actatccacg tgaaatcgct aatcagggta cgtgaaatcg ctaatcggag     2280
tacgtgaaat cgctaataag gtcacgtgaa atcgctaatc aaaaaggcac gtgagaacgc     2340
taatagccct ttcagatcaa cagcttgcaa acacccctcg ctccggcaag tagttacagc     2400
aagtagtatg ttcaattagc ttttcaatta tgaatatata tatcaattat ggtcgccct      2460 tggcttgtgg acaatgcgct acgcgcaccg gctccgcccg tggacaaccg caagcggttg     2520
cccaccgtcg agcgccagcg cctttgccca caacccggcg gccggccgca acagatcgtt     2580
ttataaattt tttttttga aaagaaaaa gcccgaaagg cggcaacctc tcgggcttct       2640
ggatttccga tcacctgtaa agtgggacca catgctgaac tccctatcac tgcatgagta     2700
gggaactgcc aggcatcaaa taaaacgaaa ggctcagtcg aaagactggg cctttcgttt     2760
tatctgttgt ttgtcggtga acgctctcct gagtaggaca aatccgccgg agcggatttt     2820
gaacgttgcg aagcaacggc ccggagggtg gcgggcagga cgcccgccat aaactgccag     2880
gcatcaaatt aagcagaagg ccatcctgac ggatggcctt tttgcgtttc tacaaactct     2940
gcaggtcgac tctagagatc taacttcggc ggcgcccgag cgtgaacagc acgggctgac     3000
caacctgtgc gcgcgcggcg gctacgtcct ggcggaagcc gaagggacgc ggcaggtcac     3060
gctggtcgcc acggggcacg aggcgatact ggcgctggcg gcacgcaaac tgttgaagga     3120
cgcaggggtt gcggcggctg tcgtatccct tccatgctgg gaactgttcg ccgcgcaaaa     3180
aatgacgtat cgtgccgccg tgctgggaac ggcaccccgg atcggcattg aagccgcgtc     3240
agggtttgga tgggaacgct ggcttgggac agacgggctg tttgttggca ttgacgggt      3300 cgggacggcc gccccggacc agccggacag cgcgactgac atcacgccgg aacggatctg     3360
```

```
ccgcgacgcg ctgcgtctgg tccgtccect gtccgatacc ctgactgaac cggcgggagg    3420
aaacggcgcg ccgcccggga tgacatcggc cgatgtcagt gtgtgaagat ctcccgggta    3480
ccgagctctc tagaaagaag gagggacgag ctattgatgg agaaaaaaat cactggatat    3540
accaccgttg atatatccca atggcatcgt aaagaacatt ttgaggcatt tcagtcagtt    3600
gctcaatgta cctataacca gaccgttcag ctggatatta cggcctttt aaagaccgta    3660 aagaaaaata agcacaagtt ttatccggcc tttattcaca ttcttgcccg cctgatgaat    3720
gctcatccgg aattccgtat ggcaatgaaa acggtgagc tggtgatatg ggatagtgtt    3780
cacccttgtt acaccgtttt ccatgagcaa actgaaacgt tttcatcgct ctggagtgaa    3840
taccacgacg atttccggca gtttctacac atatattcgc aagatgtggc gtgttacggt    3900
gaaaacctgg cctatttccc taaagggttt attgagaata tgtttttcgt ctcagccaat    3960
ccctgggtga gtttcaccag ttttgattta aacgtggcca atatggacaa cttcttcgcc    4020
cccgttttca ccatgggcaa atattatacg caaggcgaca aggtgctgat gccgctggcg    4080
attcaggttc atcatgccgt ttgtgatggc ttccatgtcg gcagaatgct taatgaatta    4140
caacagtact gcgatgagtg gcagggcggg gcgtaatttt tttaaggcag ttattggtgc    4200
ccttaaacgc ctggttgcta cgcctgaata agtgataata agcggatgaa tggcagaaat    4260
tcgtcgaggc ggcacctcgc taacggattc accactccaa gaattggagc caatcaattc    4320
ttgcggagaa ctgtgaatgc gcaaaccaac ccttggcaga acatatccat cgcgtccgcc    4380
atctccagca gccgcacgcg cgcatctcg gctgttttgg cggatgagag aagattttca    4440
gcctgataca gattaaatca gaacgcagaa gcggtctgat aaaacagaat ttgcctggcg    4500
gcagtagcgc ggtggtccca cctgacccca tgccgaactc agaagtgaaa cgccgtagcg    4560
ccgatggtag tgtggggtct ccccatgcga gagtagggaa ctgccaggca tcaaataaaa    4620
cgaaaggctc agtcgaaaga ctgggccttt cgttttatct gttgtttgtc ggtgaacgct    4680
ctcctgagta ggacaaatcc gccgggagcg gatttgaacg ttgcgaagca acggcccgga    4740
gggtggcggg caggacgccc gccataaact gccaggcatc aaattaagca gaaggccatc    4800 ctgacgatg gccttttgc gtttctacaa actcttcctg tcg                       4843
```

<210> SEQ ID NO 16
<211> LENGTH: 660
<212> TYPE: DNA
<213> ORGANISM: Artificial Sequence
<220> FEATURE:
<223> OTHER INFORMATION: Synthetic CAT gene seqeunce

<400> SEQUENCE: 16

```
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttatcc ggcctttatt    180 cacattcttg cccgcctgat gaatgctcat ccggagttcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgcccccgtt ttcactatgg gcaaatatta tacgcaaggc    540
```

```
gacaaggtgc tgatgccgct ggcgattcag gttcatcatg ccgtctgtga tggcttccat      600
gtcggcagaa tgcttaatga attacaacag tactgcgatg agtggcaggg cggggcgtaa      660

<210> SEQ ID NO 17
<211> LENGTH: 24
<212> TYPE: DNA
<213> ORGANISM: Artificial Sequence
<220> FEATURE:
<223> OTHER INFORMATION: Synthetic SeqF primer

<400> SEQUENCE: 17 atgttctttta cgatgccatt ggga                                            24

<210> SEQ ID NO 18
<211> LENGTH: 22
<212> TYPE: DNA
<213> ORGANISM: Artificial Sequence
<220> FEATURE:
<223> OTHER INFORMATION: Synthetic SeqR primer

<400> SEQUENCE: 18
tctcctgagt aggacaaatc cg                                               22

<210> SEQ ID NO 19
<211> LENGTH: 1141
<212> TYPE: DNA
<213> ORGANISM: Artificial Sequence
<220> FEATURE:
<223> OTHER INFORMATION: Synthetic P1 primer

<400> SEQUENCE: 19
gatcgcgggc acgcgctgca ttgaccgcca gcgcggcggc agccgttttg gcgcccaccg       60
caccggactt gcgctggctg accgggtgag cgggcgcgca gccgccctgt ccagcacggg      120
gcagcagaag gcgctgctgc tgggcatcgt gctgtcgcat gcgcgcatac tcgcggcatg      180
ccgggggcag gtgcccatgc tcctgctcga tgagccgctg gtgcatctgg acgaagcccg      240
caggcaggcc ctgttccgcg ccgtgggccg catgcgcacg ggcgtgttcc tgaccggaac      300
ggacgccgaa cagttcgccc ccctgcgggg ccatgccgca ttcgaggcgc aggggcggg      360 taatcttgcc catgaggcct gatttgcgtg gggaatgctg gttccgacgg gcggttgggg      420
ctataatgca ttctgatatt tgttgttat ccgctgtgga gcatctgccg gcatgtccga      480
tcaatccagt cccgatcaga aacacgatgc cgaggccaag ggcacagtag cgcccgcgcc      540
tgattatgat gaggcatcca tctcggtgct gcggggcctg gatgcggtgc gcaagcgccc      600
cggcatgtat attggcgata ccgatgacgg ctcgggcctg caccacatgg ccttcgaaat      660
cattgataac gcggtggatg aggcgcaggc cggtttcgcc accggctgcg tcgtcacccc      720
caatggcgat ggcagcgtga ccgtgcgcga tgacgggcgc ggcattccca ccggcatgca      780
ccatgaggaa ggggtgagtg cggcggaagt cgtgctgacc aagctgcatg cgggcggcaa      840
gttcaaccag aattcctaca aggttccgg tggcctgcat ggcgtgggcg ctgcggtggt      900
caatgctttg tccgaatgga tggaagtgcg catctggcgc gatggcaagg agcatgtgat      960 ccgcttcag gcggcgagc gtgatgaggc gctgcgcgtg gtgggcgaaa gtgctgagcc      1020
gcgcggcacg caggtcacat tcaagcccag tgccaagacc ttcgccaagg tggagttcga      1080
gttcccgatt ctcgagcgcc gcctgcgcga actggcctc ctcaattccg ggctcaggat      1140
c                                                                    1141
```

<210> SEQ ID NO 20
<211> LENGTH: 1058
<212> TYPE: DNA
<213> ORGANISM: Artificial Sequence
<220> FEATURE:
<223> OTHER INFORMATION: Synthetic P2 primer

<400> SEQUENCE: 20

```
gatcggtcca cgtatcaata aactgtgcgg actggtagag ggccatcccg ttctccattg      60
tttttcatcg gctggctggg ctgttaaata acctttagca tgcatcttat gtggcggcac     120
atccatcccc catgcagcat gctataatcc tgtgcttttt ccccacctgt gggtattgct     180
tcccatgcgg ggcaggtaga ttatttatga gggcatctgt cacaagccaa catcttttca     240
gtacagaatt aaattttttca tacttattaa tgtaaaatgt aatttatatt cctgttttat     300
ccatattgaa attattggat gtagaaaata acaaatttat aaatagcata acaggggttcg    360
ttttatagga aaatattcat tgaaacgttt tgcgaaaata acgtaacgat taaaaaacaa     420
taaaagttt ttcaatgcag ctttgtcaaa aaaacttat cggatactgg cagttgattg       480
aaggggttgt tcacaaaacc cgccattatc ccgtttcctg cctgcctttg gcgtgccggg     540
tagcatgatg cggacagcat gtaactgaaa ggactgtctt tcagtctgga gaacgaagcg     600
tcagcgactg gtcaactgtt tgtgtcacaa tggcattcag cgcgccatgt gctgctgtcc     660
attgaaaggg atcggcatcg ttattgaagg tcggtcaag ctggtcgccc cgtaccgtgc      720
cataggcctg aaaatacatg tcgggccggg cggggatggt gtccatcgtc catgtccagt     780
catcggacag gagagctgta gcgcctacct gcgcgcaggg gcgcgtgggt gacagggtca     840
cggctgccgt cgtcatgagg gctgcctgcg ggcggtggta gcggctgtct ccgccaatat     900
cttccatctg caggtcgcgg cggcgcgctt cctcggcggg cgggatgttg cgccagccat     960
cgccatcggg gcctgcgtgg gcgcggtcga gcgggtccga tgcagggcca aaggcgtggc    1020
ctgcgtaatt gagcgcggtg cctgcgggca catggatc                            1058
```

<210> SEQ ID NO 21
<211> LENGTH: 535
<212> TYPE: DNA
<213> ORGANISM: Artificial Sequence
<220> FEATURE:
<223> OTHER INFORMATION: Synthetic P3 primer

<400> SEQUENCE: 21

```
aacttcggcg gcgcccgagc gtgaacagca cgggctgacc aacctgtgcg cgcgcggcgg      60
ctacgtcctg gcggaagccg aagggacgcg gcaggtcacg ctggtcgcca cggggcacga    120
ggcgatactg gcgctggcgg cacgcaaact gttgaaggac gcaggggttg cggcggctgt    180
cgtatccctt ccatgctggg aactgttcgc gcgcaaaaa atgacgtatc gtgccgccgt     240
gctgggaacg gcaccccgga tcggcattga agccgcgtca gggtttggat gggaacgctg    300
gcttgggaca gacgggctgt tgttggcat tgacgggttc gggacggccg ccccggacca    360
gccggacagc gcgactgaca tcacgccgga acggatctgc gcgacgcgc tgcgtctggt     420
ccgtcccctg tccgatacccc tgactgaacc ggcgggagga acggcgcgc cgcccgggat    480
gacatcggcc gatgtcagtg tgtgaaatgt cagaccttac ggagaaaata agaaa         535
```

<210> SEQ ID NO 22
<211> LENGTH: 35
<212> TYPE: DNA
<213> ORGANISM: Artificial Sequence
<220> FEATURE:

<223> OTHER INFORMATION: Synthetic Puc19 vector1 F Primer

<400> SEQUENCE: 22
acacggtgcc tgactgcgtt agcaatttaa ctgtg 35

<210> SEQ ID NO 23
<211> LENGTH: 43
<212> TYPE: DNA
<213> ORGANISM: Artificial Sequence
<220> FEATURE:
<223> OTHER INFORMATION: Synthetic Puc19 vector1 R Primer

<400> SEQUENCE: 23
atggaagccg gcggcacctc gctaacggat tcaccactcc aag 43

<210> SEQ ID NO 24
<211> LENGTH: 51
<212> TYPE: DNA
<213> ORGANISM: Artificial Sequence
<220> FEATURE:
<223> OTHER INFORMATION: Synthetic Tetracyclin F Primer

<400> SEQUENCE: 24
cgcagtcagg caccgtgtat gaaatctaac aatgcgctca tcgtcatcct c 51

<210> SEQ ID NO 25
<211> LENGTH: 44
<212> TYPE: DNA
<213> ORGANISM: Artificial Sequence
<220> FEATURE:
<223> OTHER INFORMATION: Synthetic Tetracyclin R primer

<400> SEQUENCE: 25
ggtgccgccg gcttccattc aggtcgaggt ggcccggctc catg 44

<210> SEQ ID NO 26
<211> LENGTH: 34
<212> TYPE: DNA
<213> ORGANISM: Artificial Sequence
<220> FEATURE:
<223> OTHER INFORMATION: Synthetic pUC19-Tet vector 2F primer

<400> SEQUENCE: 26
atcacctgta agtcggacga attcggcgct cttc 34

<210> SEQ ID NO 27
<211> LENGTH: 42
<212> TYPE: DNA
<213> ORGANISM: Artificial Sequence
<220> FEATURE:
<223> OTHER INFORMATION: Synthetic pUC19-tet vector 2R primer

<400> SEQUENCE: 27
atcgctgtct tgctggctga attcgaattt ctgccattca tc 42

<210> SEQ ID NO 28
<211> LENGTH: 41
<212> TYPE: DNA
<213> ORGANISM: Artificial Sequence
<220> FEATURE:
<223> OTHER INFORMATION: Synthetic pSa ori F primer

<400> SEQUENCE: 28
gccagcaaga cagcgataga gggtagttat ccacgtgaaa c 41

<210> SEQ ID NO 29
<211> LENGTH: 41
<212> TYPE: DNA
<213> ORGANISM: Artificial Sequence
<220> FEATURE:
<223> OTHER INFORMATION: Synthetic pSa ori R primer

<400> SEQUENCE: 29
cgacttacag gtgatcggaa atccagaagc cgagaggtt g                 41

<210> SEQ ID NO 30
<211> LENGTH: 45
<212> TYPE: DNA
<213> ORGANISM: Artificial Sequence
<220> FEATURE:
<223> OTHER INFORMATION: Synthetic pTsa EX1 vector primer F

<400> SEQUENCE: 30
ctgacggatg gcctttttgc cttccgcttc ctcgctcact gactc            45

<210> SEQ ID NO 31
<211> LENGTH: 44
<212> TYPE: DNA
<213> ORGANISM: Artificial Sequence
<220> FEATURE:
<223> OTHER INFORMATION: Synthetic pTsa EX1 vector primer R

<400> SEQUENCE: 31
tctacgccgg acgcatcgcg tccgacttac aggtgatcgg aaat             44

<210> SEQ ID NO 32
<211> LENGTH: 39
<212> TYPE: DNA
<213> ORGANISM: Artificial Sequence
<220> FEATURE:
<223> OTHER INFORMATION: Synthetic tac promoter primer(f)

<400> SEQUENCE: 32
cgatgcgtcc ggcgtagagg atccggagct tatcgactg                   39

<210> SEQ ID NO 33
<211> LENGTH: 55
<212> TYPE: DNA
<213> ORGANISM: Artificial Sequence
<220> FEATURE:
<223> OTHER INFORMATION: Synthetic tac promoter primer R

<400> SEQUENCE: 33
cgagctcggt acccaatcaa tagctcgtcc ctgtgtgaaa ttgttatccg ctcac  55

<210> SEQ ID NO 34
<211> LENGTH: 48
<212> TYPE: DNA
<213> ORGANISM: Artificial Sequence
<220> FEATURE:
<223> OTHER INFORMATION: Synthetic RBS MCS primer F

<400> SEQUENCE: 34
attgggtacc gagctcgaat tcgtacccgg ggatcctcta gagtcgac         48

<210> SEQ ID NO 35
<211> LENGTH: 27
<212> TYPE: DNA
<213> ORGANISM: Artificial Sequence
<220> FEATURE:
<223> OTHER INFORMATION: Synthetic terminator primer R

<400> SEQUENCE: 35
gcaaaaaggc catccgtcag gatggcc                                27

<210> SEQ ID NO 36
<211> LENGTH: 45
<212> TYPE: DNA
<213> ORGANISM: Artificial Sequence
<220> FEATURE:
<223> OTHER INFORMATION: Synthetic GapA vector primer F

<400> SEQUENCE: 36
ctgacggatg gcctttttgc cttccgcttc ctcgctcact gactc             45

<210> SEQ ID NO 37
<211> LENGTH: 44
<212> TYPE: DNA
<213> ORGANISM: Artificial Sequence
<220> FEATURE:
<223> OTHER INFORMATION: Synthetic GapA vector primer R

<400> SEQUENCE: 37
cgggcgccgc cgaagttgcg tccgacttac aggtgatcgg aaat              44

<210> SEQ ID NO 38
<211> LENGTH: 31
<212> TYPE: DNA
<213> ORGANISM: Artificial Sequence
<220> FEATURE:
<223> OTHER INFORMATION: Synthetic GapA promoter primer F

<400> SEQUENCE: 38
aacttcggcg gcgcccgagc gtgaacagca c                            31

<210> SEQ ID NO 39
<211> LENGTH: 44
<212> TYPE: DNA
<213> ORGANISM: Artificial Sequence
<220> FEATURE:
<223> OTHER INFORMATION: Synthetic GapA promoter primer R

<400> SEQUENCE: 39
cgagctcggt acccaatttt cttattttct ccgtaaggtc tgac              44

<210> SEQ ID NO 40
<211> LENGTH: 45
<212> TYPE: DNA
<213> ORGANISM: Artificial Sequence
<220> FEATURE:
<223> OTHER INFORMATION: Synthetic bla promoter F

<400> SEQUENCE: 40
gtatccgctc atgagacaat tgtggaattg tgagcggata acaat             45

<210> SEQ ID NO 41
<211> LENGTH: 51
<212> TYPE: DNA
<213> ORGANISM: Artificial Sequence
<220> FEATURE:
<223> OTHER INFORMATION: Synthetic bla promoter R

<400> SEQUENCE: 41
attgtctcat gagcggatac atatttgaaa tttcagaata tttgccagaa c       51

<210> SEQ ID NO 42
<211> LENGTH: 1395

<212> TYPE: DNA
<213> ORGANISM: Escherichia coli
<220> FEATURE:
<221> NAME/KEY: CDS
<222> LOCATION: (1)..(1395)
<223> OTHER INFORMATION: Escherichia coli galP gene

<400> SEQUENCE: 42

```
atg cct gac gct aaa aaa cag ggg cgg tca aac aag gca atg acg ttt      48
Met Pro Asp Ala Lys Lys Gln Gly Arg Ser Asn Lys Ala Met Thr Phe
 1               5                  10                  15 ttc gtc tgc ttc ctt gcc gct ctg gcg gga tta ctc ttt ggc ctg gat      96
Phe Val Cys Phe Leu Ala Ala Leu Ala Gly Leu Leu Phe Gly Leu Asp
             20                  25                  30 atc ggt gta att gct ggc gca ctg ccg ttt att gca gat gaa ttc cag     144
Ile Gly Val Ile Ala Gly Ala Leu Pro Phe Ile Ala Asp Glu Phe Gln
         35                  40                  45 att act tcg cac acg caa gaa tgg gtc gta agc tcc atg atg ttc ggt     192
Ile Thr Ser His Thr Gln Glu Trp Val Val Ser Ser Met Met Phe Gly
     50                  55                  60 gcg gca gtc ggt gcg gtg ggc agc ggc tgg ctc tcc ttt aaa ctc ggg     240
Ala Ala Val Gly Ala Val Gly Ser Gly Trp Leu Ser Phe Lys Leu Gly
 65                  70                  75                  80 cgc aaa aag agc ctg atg atc ggc gca att ttg ttt gtt gcc ggt tcg     288
Arg Lys Lys Ser Leu Met Ile Gly Ala Ile Leu Phe Val Ala Gly Ser
                 85                  90                  95 ctg ttc tct gcg gct gcg cca aac gtt gaa gta ctg att ctt tcc cgc     336
Leu Phe Ser Ala Ala Ala Pro Asn Val Glu Val Leu Ile Leu Ser Arg
            100                 105                 110 gtt cta ctg ggg ctg gcg gtg ggt gtg gcc tct tat acc gca ccg ctg     384
Val Leu Leu Gly Leu Ala Val Gly Val Ala Ser Tyr Thr Ala Pro Leu
        115                 120                 125 tac ctc tct gaa att gcg ccg gaa aaa att cgt ggc agt atg atc tcg     432
Tyr Leu Ser Glu Ile Ala Pro Glu Lys Ile Arg Gly Ser Met Ile Ser
    130                 135                 140 atg tat cag ttg atg atc act atc ggg atc ctc ggt gct tat ctt tct     480
Met Tyr Gln Leu Met Ile Thr Ile Gly Ile Leu Gly Ala Tyr Leu Ser
145                 150                 155                 160 gat acc gcc ttc agc tac acc ggt gca tgg cgc tgg atg ctg ggt gtg     528
Asp Thr Ala Phe Ser Tyr Thr Gly Ala Trp Arg Trp Met Leu Gly Val
                165                 170                 175 att atc atc ccg gca att ttg ctg ctg att ggt gtc ttc ttc ctg cca     576
Ile Ile Ile Pro Ala Ile Leu Leu Leu Ile Gly Val Phe Phe Leu Pro
            180                 185                 190 gac agc cca cgt tgg ttt gcc gcc aaa cgc cgt ttt gtt gat gcc gaa     624
Asp Ser Pro Arg Trp Phe Ala Ala Lys Arg Arg Phe Val Asp Ala Glu
        195                 200                 205 cgc gtg ctg cta cgc ctg cgt gac acc agc gcg gaa gcg aaa cgc gaa     672
Arg Val Leu Leu Arg Leu Arg Asp Thr Ser Ala Glu Ala Lys Arg Glu
    210                 215                 220 ctg gat gaa atc cgt gaa agt ttg cag gtt aaa cag agt ggc tgg gcg     720
Leu Asp Glu Ile Arg Glu Ser Leu Gln Val Lys Gln Ser Gly Trp Ala
225                 230                 235                 240 ctg ttt aaa gag aac agc aac ttc cgc cgc gcg gtg ttc ctt ggc gta     768
Leu Phe Lys Glu Asn Ser Asn Phe Arg Arg Ala Val Phe Leu Gly Val
                245                 250                 255 ctg ttg cag gta atg cag caa ttc acc ggg atg aac gtc atc atg tat     816
Leu Leu Gln Val Met Gln Gln Phe Thr Gly Met Asn Val Ile Met Tyr
            260                 265                 270 tac gcg ccg aaa atc ttc gaa ctg gcg ggt tat acc aac act acc gag     864
Tyr Ala Pro Lys Ile Phe Glu Leu Ala Gly Tyr Thr Asn Thr Thr Glu
```

| | | | | | | | | | | | | | | | | |
|---|---|---|---|---|---|---|---|---|---|---|---|---|---|---|---|---|
| | | 275 | | | | 280 | | | | | 285 | | | | | |
| caa | atg | tgg | ggg | acc | gtg | att | gtc | ggc | ctg | acc | aac | gta | ctt | gcc | acc | 912 |
| Gln | Met | Trp | Gly | Thr | Val | Ile | Val | Gly | Leu | Thr | Asn | Val | Leu | Ala | Thr | |
| | 290 | | | | | 295 | | | | 300 | | | | | | |
| ttt | atc | gca | atc | ggc | ctt | gtt | gac | cgc | tgg | gga | cgt | aaa | cca | acg | cta | 960 |
| Phe | Ile | Ala | Ile | Gly | Leu | Val | Asp | Arg | Trp | Gly | Arg | Lys | Pro | Thr | Leu | |
| 305 | | | | | 310 | | | | | 315 | | | | | 320 | |
| acg | ctg | ggc | ttc | ctg | gtg | atg | gct | gct | ggc | atg | ggc | gta | ctc | ggt | aca | 1008 |
| Thr | Leu | Gly | Phe | Leu | Val | Met | Ala | Ala | Gly | Met | Gly | Val | Leu | Gly | Thr | |
| | | | | 325 | | | | | 330 | | | | | 335 | | |
| atg | atg | cat | atc | ggt | att | cac | tct | ccg | tcg | gcg | cag | tat | ttc | gcc | atc | 1056 |
| Met | Met | His | Ile | Gly | Ile | His | Ser | Pro | Ser | Ala | Gln | Tyr | Phe | Ala | Ile | |
| | | | 340 | | | | | 345 | | | | | 350 | | | |
| gcc | atg | ctg | ctg | atg | ttt | att | gtc | ggt | ttt | gcc | atg | agt | gcc | ggt | ccg | 1104 |
| Ala | Met | Leu | Leu | Met | Phe | Ile | Val | Gly | Phe | Ala | Met | Ser | Ala | Gly | Pro | |
| | | | 355 | | | | | 360 | | | | | 365 | | | |
| ctg | att | tgg | gta | ctg | tgc | tcc | gaa | att | cag | ccg | ctg | aaa | ggc | cgc | gat | 1152 |
| Leu | Ile | Trp | Val | Leu | Cys | Ser | Glu | Ile | Gln | Pro | Leu | Lys | Gly | Arg | Asp | |
| | 370 | | | | | 375 | | | | | 380 | | | | | |
| ttt | ggc | atc | acc | tgc | tcc | act | gcc | acc | aac | tgg | att | gcc | aac | atg | atc | 1200 |
| Phe | Gly | Ile | Thr | Cys | Ser | Thr | Ala | Thr | Asn | Trp | Ile | Ala | Asn | Met | Ile | |
| 385 | | | | | 390 | | | | | 395 | | | | | 400 | |
| gtt | ggc | gca | acg | ttc | ctg | acc | atg | ctc | aac | acg | ctg | ggt | aac | gcc | aac | 1248 |
| Val | Gly | Ala | Thr | Phe | Leu | Thr | Met | Leu | Asn | Thr | Leu | Gly | Asn | Ala | Asn | |
| | | | | 405 | | | | | 410 | | | | | 415 | | |
| acc | ttc | tgg | gtg | tat | gcg | gct | ctg | aac | gta | ctg | ttt | atc | ctg | ctg | aca | 1296 |
| Thr | Phe | Trp | Val | Tyr | Ala | Ala | Leu | Asn | Val | Leu | Phe | Ile | Leu | Leu | Thr | |
| | | | 420 | | | | | 425 | | | | | 430 | | | |
| ttg | tgg | ctg | gta | ccg | gaa | acc | aaa | cac | gtt | tcg | ctg | gaa | cat | att | gaa | 1344 |
| Leu | Trp | Leu | Val | Pro | Glu | Thr | Lys | His | Val | Ser | Leu | Glu | His | Ile | Glu | |
| | | 435 | | | | | 440 | | | | | 445 | | | | |
| cgt | aat | ctg | atg | aaa | ggt | cgt | aaa | ctg | cgc | gaa | ata | ggc | gct | cac | gat | 1392 |
| Arg | Asn | Leu | Met | Lys | Gly | Arg | Lys | Leu | Arg | Glu | Ile | Gly | Ala | His | Asp | |
| | 450 | | | | | 455 | | | | | 460 | | | | | |
| taa | | | | | | | | | | | | | | | | 1395 |

<210> SEQ ID NO 43
<211> LENGTH: 33
<212> TYPE: DNA
<213> ORGANISM: Artificial Sequence
<220> FEATURE:
<223> OTHER INFORMATION: Synthetic BcsA primer F

<400> SEQUENCE: 43
atgtcagagg ttcagtcgcc agtacccgcg gag          33

<210> SEQ ID NO 44
<211> LENGTH: 30
<212> TYPE: DNA
<213> ORGANISM: Artificial Sequence
<220> FEATURE:
<223> OTHER INFORMATION: Synthetic BcsA primer R

<400> SEQUENCE: 44
gccaggccac tggccacagg aatgcgcaag          30

<210> SEQ ID NO 45
<211> LENGTH: 31
<212> TYPE: DNA
<213> ORGANISM: Artificial Sequence
<220> FEATURE:
<223> OTHER INFORMATION: Synthetic tetracyclin F

```
<400> SEQUENCE: 45
atgaaatcta acaatgcgct catcgtcatc c                              31

<210> SEQ ID NO 46
<211> LENGTH: 31
<212> TYPE: DNA
<213> ORGANISM: Artificial Sequence
<220> FEATURE:
<223> OTHER INFORMATION: Synthetic tetracyclin R

<400> SEQUENCE: 46
cgaaaatgac ccagagcgct gccggcacct g                              31

<210> SEQ ID NO 47
<211> LENGTH: 57
<212> TYPE: DNA
<213> ORGANISM: Artificial Sequence
<220> FEATURE:
<223> OTHER INFORMATION: Synthetic galP primer F

<400> SEQUENCE: 47
cctctagagt cgaccatgcc tgacgctaaa aaacaggggc ggtcaaacaa ggcaatg   57

<210> SEQ ID NO 48
<211> LENGTH: 58
<212> TYPE: DNA
<213> ORGANISM: Artificial Sequence
<220> FEATURE:
<223> OTHER INFORMATION: Synthetic galP primer R

<400> SEQUENCE: 48
ccaagcttgc atgccttaat cgtgagcgcc tatttcgcgc agtttacgac ctttcatc  58
```